(12) United States Patent
Jacovella et al.

(10) Patent No.: US 10,206,939 B2
(45) Date of Patent: *Feb. 19, 2019

(54) TREATMENT OF PAPULOPUSTULAR ROSACEA WITH IVERMECTIN

(71) Applicant: Galderma S.A., Cham (CH)

(72) Inventors: Jean Jacovella, Antibes (FR); Jean-Paul Chappuis, Valbonne (FR); Alexandre Kaoukhov, Newport Beach, CA (US); Michael Graeber, Lawrenceville, NJ (US); Michel Poncet, Mougins (FR); Philippe Briantais, Antibes (FR); Laurence Salin, La Roquette sur Siagne (FR)

(73) Assignee: Galderma S.A., Cham (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/988,368

(22) Filed: May 24, 2018

(65) Prior Publication Data

US 2018/0264021 A1 Sep. 20, 2018

Related U.S. Application Data

(63) Continuation of application No. 15/909,090, filed on Mar. 1, 2018, which is a continuation of application No. 14/973,037, filed on Dec. 17, 2015, now abandoned, which is a continuation of application No. 14/209,958, filed on Mar. 13, 2014, now Pat. No. 9,233,118.

(60) Provisional application No. 61/927,717, filed on Jan. 15, 2014, provisional application No. 61/919,208, filed on Dec. 20, 2013, provisional application No. 61/843,540, filed on Jul. 8, 2013.

(51) Int. Cl.

| A61K 9/06 | (2006.01) |
| A61P 17/00 | (2006.01) |
| A61P 33/14 | (2006.01) |
| A61K 31/7048 | (2006.01) |
| A61K 31/4174 | (2006.01) |
| A61K 9/00 | (2006.01) |
| A61K 31/4164 | (2006.01) |
| A61K 47/10 | (2017.01) |
| A61K 47/14 | (2017.01) |
| A61K 47/02 | (2006.01) |
| A61K 47/12 | (2006.01) |
| A61K 47/18 | (2017.01) |
| A61K 47/24 | (2006.01) |
| A61K 47/26 | (2006.01) |
| A61K 47/32 | (2006.01) |

(52) U.S. Cl.
CPC ........ *A61K 31/7048* (2013.01); *A61K 9/0014* (2013.01); *A61K 9/06* (2013.01); *A61K 31/4164* (2013.01); *A61K 31/4174* (2013.01); *A61K 47/02* (2013.01); *A61K 47/10* (2013.01); *A61K 47/12* (2013.01); *A61K 47/14* (2013.01); *A61K 47/183* (2013.01); *A61K 47/24* (2013.01); *A61K 47/26* (2013.01); *A61K 47/32* (2013.01); *A61P 17/00* (2018.01); *A61P 33/14* (2018.01)

(58) Field of Classification Search
CPC .................................................. A61K 31/7048
See application file for complete search history.

(56) References Cited

U.S. PATENT DOCUMENTS

| 5,332,577 A | 7/1994 | Gertner et al. |
| 5,656,280 A | 8/1997 | Herb et al. |
| 5,952,372 A | 9/1999 | McDaniel |
| 6,133,310 A | 10/2000 | Parks |
| 6,136,328 A | 10/2000 | Sebillotte-Arnaud et al. |
| 6,319,945 B1 | 11/2001 | Parks |
| 6,399,651 B1 | 6/2002 | Parks |
| 6,399,652 B1 | 6/2002 | Parks |
| 6,433,006 B2 | 8/2002 | Parks |
| 6,458,342 B1 | 10/2002 | Heidenfelder et al. |
| 7,550,440 B2 | 6/2009 | Manetta et al. |
| 8,080,530 B2 | 12/2011 | Manetta et al. |
| 8,093,219 B2 | 1/2012 | Manetta et al. |
| 8,415,311 B2 | 4/2013 | Manetta et al. |
| 8,470,788 B2 | 6/2013 | Manetta et al. |
| 2002/0035076 A1 | 3/2002 | Parks |
| 2002/0035161 A1 | 3/2002 | Segura et al. |
| 2002/0061855 A1 | 5/2002 | Parks |
| 2007/0116731 A1 | 5/2007 | Astruc et al. |

(Continued)

FOREIGN PATENT DOCUMENTS

| EP | 0045655 A2 | 2/1982 |
| FR | 2867684 A1 | 9/2005 |

(Continued)

OTHER PUBLICATIONS

Korting, H. et al "Current topical and systemic approaches to treatment of rosacea" J. Eur. Acad. Dermatol. Venereol., vol. 23, No. 8, pp. 876-882. (Year: 2009).*

(Continued)

*Primary Examiner* — Leigh C Maier

(74) *Attorney, Agent, or Firm* — Panitch Schwarze Belisario & Nadel LLP

(57) ABSTRACT

Methods and compositions for safe and effective treatment of papulopustular rosacea in a subject are described. The methods involve topically applying to an affected skin area a topical composition containing ivermectin and a pharmaceutically acceptable carrier. Treatment with ivermectin represents an innovative therapy that is more robust and effective than the conventional treatments.

25 Claims, 11 Drawing Sheets

(56) References Cited

U.S. PATENT DOCUMENTS

| | | |
|---|---|---|
| 2009/0233877 A1 | 9/2009 | Kaoukhov et al. |
| 2012/0077766 A1 | 3/2012 | Manetta et al. |

FOREIGN PATENT DOCUMENTS

| | | |
|---|---|---|
| JP | 2006-524212 A | 10/2006 |
| RU | 2350333 C2 | 3/2009 |
| WO | 0128555 A1 | 4/2001 |
| WO | 03032976 A1 | 4/2003 |
| WO | 03032977 A1 | 4/2003 |
| WO | 03066009 A1 | 8/2003 |
| WO | 03075656 A2 | 9/2003 |
| WO | 2004093886 A1 | 11/2004 |
| WO | 200558312 A1 | 6/2005 |
| WO | 2006097628 A1 | 9/2006 |
| WO | 2006131651 A2 | 12/2006 |
| WO | 2006131652 A1 | 12/2006 |
| WO | 2006131653 A1 | 12/2006 |
| WO | 2007071876 A1 | 6/2007 |
| WO | 2007119028 A2 | 10/2007 |
| WO | 2008043973 A1 | 4/2008 |
| WO | 2008043974 A2 | 4/2008 |
| WO | 2010072958 A2 | 7/2010 |
| WO | 2010086725 A1 | 8/2010 |
| WO | 2010092312 A1 | 8/2010 |
| WO | 2014049298 A1 | 4/2014 |

OTHER PUBLICATIONS

Holmes, "Potential role of microorganisms in the pathogenesis of rosacea," J Am Acad Dermatol, vol. 69, No. 6, pp. 1025-1032 (2013).

Ianaro et al, "Anti-inflammatory activity of macrolide antibiotics," J Pharmacol Exp Ther, vol. 292, No. 1, pp. 156-163 (2000).

Campbell, "History of avermectin and ivermectin, with notes on the history of other macrocyclic lactone antiparasitic agents," Curr Pharm Biotechnol, vol. 13, No. 6, pp. 853-865 (2012).

Forstinger et al, "Treatment of rosacea-like demodicidosis with oral ivermectin and topical permethrin cream," J Am Acad Dermatol, vol. 41, pp. 775-777 (1999).

Pariser et al, "Topical 0.5% ivermectin lotion for treatment of head lice," N Engl J Med, vol. 367, No. 18, pp. 1687-1693 (2012).

Zhang et al, "Ivermectin inhibits LPS-induced production of inflammatory cytokines and improves LPS-induced survival in mice," Inflamm Res, vol. 57, pp. 524-529 (2008).

Van Zuuren et al, "Effective and evidence-based management strategies for rosacea: summary of a Cochrane systematic review," Br J Dermatol, vol. 165, No. 4, pp. 760-781 (2011).

Elewski, "Results of a national rosacea patient survey: common issues that concern rosacea sufferers," J Drugs Dermatol, vol. 8, No. 2, pp. 120-123 (2009).

Guzzo et al, "Safety, Tolerability, and Pharmacokinetics of Escalating High Doses of Ivermectin in Healthy Adult Subjects," J. Clin. Pharmacol., vol. 42, pp. 1122-1133 (2002).

Fink et al, "Pharmacokinetics of Ivermectin in Animals and Humans," Ivermectin and Abamectin, Ed. Campbell, Springer-Verlag New York Inc., pp. 113-129 (1989).

Toutain et al, "Plasma terminal half-life," J. Vet. Pharmacol. Therap., vol. 27, pp. 427-439 (2004).

Dahl et al, "Once-daily topical metronidazole cream formulations in the treatment of the papules and pustules of rosacea," J Am. Acad. Dermatol., pp. 723-730 (Nov. 2001).

Thiboutot et al, "Efficacy and safety of azelaic acid (15%) gel as a new treatment for papulopustular rosacea: Results from two vehicle-controlled, randomized phase III studies," J Am Acad Dermatol, vol. 48, No. 6, pp. 836-845 (Jun. 2003).

Canga et al, "The pharmacokinetics and metabolism of ivermectin in domestic animcal species," The Veterinary Journal, vol. 179, No. 1, pp. 25-37 (2009).

Canga et al, "The Pharmacokinetics and Interactions of Ivermectin in Humans—A Mini-review," The AAPS Journal, vol. 10, No. 1, pp. 42-46 (Mar. 2008).

Victoria, et al., "Topical Ivermectin: A New Successful Treatment for Scabies" Pediatric Dermatology, 2001, pp. 63-65, vol. 18, No. 1.

"Cetaphil cleansers and moisturizers" Online! 2004, XP002287576; Retrieved from the Internet:URL:http://www.cetaphil.com/product.sub.-information/moisturizers.cfm; retrieved on Jul. 8, 2004.

Rebora, "The Management of Rosacea", Am. J. Clin. Dermatol., vol. 3, No. 7, pp. 489-496 (2002).

Gold et al, "Efficacy and safety of ivermectin 1% cream in treatment of papulopustular rosacea: results of two randomized, double-blind, vehicle-controlled pivotal studies," Journal of Drugs in Dermatology, vol. 13, No. 3, pp. 316-323 (2014).

Taib et al. "Superiority of ivermectin 1% cream over metronidazole 0.75% cream in treating inflammatory lesions of rosacea: a randomized, investigator-blinded trial." Br J Dermatol. Sep. 16, 2014.

Allen et al. "Recalcitrant papulopustular rosacea in an immunocompetent patient responding to combination therapy with oral ivermectin and topical permethrin." Cutis. Aug. 2007;80(2):149-51.

Salem et al. "Evaluation of the efficacy of oral ivermectin in comparison with ivermectin-metronidazole combined therapy in the treatment of ocular and skin lesions of Demodex folliculorum" International Journal of Infectious Diseases (2013) 17(5), e343-e347.

Int'l Search Report dated Sep. 24, 2014 in Int'l Application No. PCT/US2014/045717.

International Search Report for corresponding PCT/US2014/45739 dated Sep. 24, 2014.

Millikan, The Proposed Inflammatory Pathophysiology of Rosacea: Implications for Treatment; Skinmed. 2003;2(1).

Loo et al, "Ivermectin cream in rosacea: comparison with metronidazole gel," British Journal of Dermatology, vol. 151, Supp. 68, p. 61 (2004).

Stankiewicz et al, "Influence of ivermectin on cellular and humoral immune responses of lambs," Veterinary Immunology and Immunopathy, vol. 44, pp. 347-358 (1995).

Forton "Papulopustular Rosacea, Skin Immunity and Demodex: Pityriasis Folliculorum as a Missing Link"; Journal of te European Academy of Dermatology and Venereology (2012), 26, 19-28.

Finacea (azelaic acid) gel, 15%, label (Jul. 2010).

Merck Manuals (18th edition), Japanese version (1st edition), pp. 991 (2006).

Wilkin et al., "Standard Grading System for Rosacea: Report of the National Rosacea Society Expert of Committee on the Classification and Staging of Rosacea", J. Am Acad Dermatol., vol. 50, pp. 907-912 (2004).

EU Clinical trials Register, downloaded from webpage: https://www.clinicaltrialregister.eu/ctr-search/trial/2008-002679-29/DE, Sep. 2017.

Clinical Trials, View of NCT01493947, downloaded from website, https://clinicaltrials.gov/archive/NCT01493947/2002_04_19, Apr. 19, 2012.

Rosacea Support Group, More Proof that CD5024 is Ivermectin, downloaded from website, https://rosacea-support.org/more-proof-that-cd5024-is-ivermectin.html, dated Oct. 23, 2017.

Wade et al., "Handbook of Pharmaceutical Excipients", Second Edition, Washington: American Pharmaceutical Association, 1994.

Gennaro, Remington: The Science and Practice of Pharmacy, 19th Edition, Easton, PA: Mack Publishing, 1995.

United States Pharmacopeial Convention, The United States Pharmacopeia, the National Formulary: USP 23, NF 18, 1995.

\* cited by examiner

** p<.001

* p<.01, ** p<.001

* p<.01, ** p<.001

IGA= 4; IL= 63                    IGA= 1; IL= 2

* $p<.05$, ** $p<.001$

*$p<.05$, ** $p<.001$

TREATMENT OF PAPULOPUSTULAR ROSACEA WITH IVERMECTIN

CROSS-REFERENCE TO RELATED APPLICATIONS

This application a continuation of U.S. patent application Ser. No. 15/909,090, filed Mar. 1, 2018, which is a continuation of U.S. patent application Ser. No. 14/973,037, filed Dec. 17, 2015, abandoned Mar. 8, 2018, which is a continuation of U.S. patent application Ser. No. 14/209,958, filed Mar. 13, 2014, issued as U.S. Pat. No. 9,233,118 on Jan. 12, 2016, which is entitled to priority pursuant to 35 U.S.C. § 119(e) to U.S. Provisional Patent Application No. 61/843,540, filed Jul. 8, 2013, U.S. Provisional Patent Application No. 61/919,208 filed Dec. 20, 2013, and U.S. Provisional Patent Application No. 61/927,717, filed Jan. 15, 2014, the disclosure of each of which is hereby incorporated by reference herein in its entirety.

BACKGROUND OF THE INVENTION

Papulopustular rosacea (PPR) is a chronic inflammatory disorder characterized by facial papules, pustules, and persistent erythema.[1] It is highly prevalent and associated with adverse impact on quality of life and depression.[2] The etiology of rosacea is multifactorial. In addition to neurovascular dysregulation, the facial skin of patients with rosacea is affected by augmented proinflammatory immune responses.[3] The principal active cathelicidin peptide (LL-37) is highly concentrated in skin affected by rosacea and can contribute to acute inflammation.[4] Moreover, PPR is characterized by the presence of inflammatory infiltrates that accompany flares, along with a heightened immune response involving neutrophilic infiltration and increased gene expression of IL-8.[5] In addition to exogenous factors (including UV light, heat and alcohol), it may be triggered by *Demodex folliculorum* mites.[3] Some studies of PPR observed higher mite densities compared to controls.[6-7] Therefore, a multitude of factors can activate neurovascular and/or immune responses, and consequential inflammation leading to flares of rosacea.[3]

Inflammatory lesions of rosacea, particularly moderate to severe PPR, are difficult to treat. Only a few therapeutic alternatives currently exist in the treatment of inflammatory lesions of rosacea. In the United States, only three FDA-approved treatments are indicated for the reduction of inflammatory lesions of rosacea, including two topical treatments. A recent Cochrane review noted some evidence supporting the effectiveness of topical metronidazole and azelaic acid in the treatment of moderate to severe rosacea,[8] yet it is clear that not all patients respond to these medications. In a national survey of current rosacea medication users, 46% of patients had previously changed medications, usually due to a lack of improvement.[9]

Ivermectin is an anti-parasitic drug derivative from the macrocyclic lactones family approved for human use for treatment and chemoprophylaxis of onchocerciasis and strongyloidiasis since 1996 in the USA and since 1988 in France. In addition, it has been approved in France for the treatment of human scabies. Oral ivermectin in human and animal demodicidosis was effective in reducing *Demodex folliculorum* and improving demodicidosis. Moreover, when administered orally, ivermectin combined with a subsequent weekly application of topical permethrin showed treatment efficacy in a patient presenting chronic rosacea-like demodicidosis (14).

U.S. Pat. No. 5,952,372 discloses a method of treating rosacea in humans involving orally or topically administering ivermectin. However, according to U.S. Pat. No. 5,952,372, because of the skin barrier effect, topical treatment with ivermectin would be anticipated to require once- or twice-daily applications for as long as four weeks to achieve sufficient follicle penetration and effective miticidal activity. It further describes that after ivermectin carries out its miticidal activity on skin *Demodex folliculorum* organisms, inflammatory responses to them begin to diminish but remnants of the dead mites still elicit some flushing and lesion formation until the cleanup processes of the body remove them, a process that requires six to eight weeks. It suggests to employ conventional anti-rosacea medications, such as oral tetracycline and topical metronidazole, to suppress early flareups and to give early clinical response during the initial phase of ivermectin administration. U.S. Pat. No. 5,952,372 contains no specific disclosure on topical treatment of PPR.

U.S. Pat. No. 6,133,310 and U.S. Pat. No. 8,415,311 also disclose a method of treating acne rosacea by topical application of ivermectin. However, they contain no specific disclosure on treating inflammatory lesions of rosacea or PPR.

Accordingly, treatments demonstrated to have a greater efficacy in treating PPR, particularly moderate to severe PPR, than the currently available compositions, such as metronidazole compositions, are still needed to provide greater, longer lasting, or more rapid relief to those in need of the treatment. There is a need for improved effective treatment of PPR, particularly moderate to severe PPR. Such need is met by the present invention.

BRIEF SUMMARY OF THE INVENTION

It is now demonstrated that topical administration of ivermectin provided more rapid relief of papulopustular rosacea as well as longer period of time that is free of relapse as compared to the currently available treatments, such as the topical treatment with 0.75% by weight of metronidazole.

In one general aspect, embodiments of the present invention relate to a method of treating papulopustular rosacea in a subject in need thereof, comprising topically administering to a skin area affected by the papulopustular rosacea a therapeutically effective amount of a pharmaceutical composition comprising ivermectin and a pharmaceutically acceptable carrier.

Another general aspect of the present invention relates to a method of treating inflammatory lesions of papulopustular rosacea in a subject in need thereof, comprising topically administering to a skin area affected by the inflammatory lesions of papulopustular rosacea a pharmaceutical composition comprising ivermectin and a pharmaceutically acceptable carrier. In a preferred embodiment of the present invention, the pharmaceutical composition comprises about 0.5% to 1.5% by weight ivermectin.

In another preferred embodiment of the present invention, the subject has moderate to severe papulopustular rosacea before the treatment.

In yet another preferred embodiment of the present invention, the subject has at least 10, preferably at least 12 and more preferably at least 15, inflammatory lesions of papulopustular rosacea, before the treatment.

According to embodiments of the present invention, once daily topical treatment with ivermectin is significantly superior than twice-daily topical treatment with metronidazole in treating papulopustular rosacea.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise embodiments shown in the drawings.

FIG. 4A: at week 12 in studies 1 and 2; FIG. 4B: at weeks 2, 4, 8 and 12 in study 1; and FIG. 4C: at weeks 2, 4, 8 and 12 in study 2, wherein SOOLANTRA is a 1% ivermectin cream;

FIG. 5A: mean absolute change (±standard error) in study 1; FIG. 5B: mean absolute change (±standard error) in study 2; FIG. 5C: median percent change in study 1; and FIG. 5D: median percent change in study 2, wherein SOOLANTRA is a 1% ivermectin cream;

FIG. 6A: Study 1 and FIG. 6B: Study 2;

DETAILED DESCRIPTION OF THE INVENTION

Figure 1:
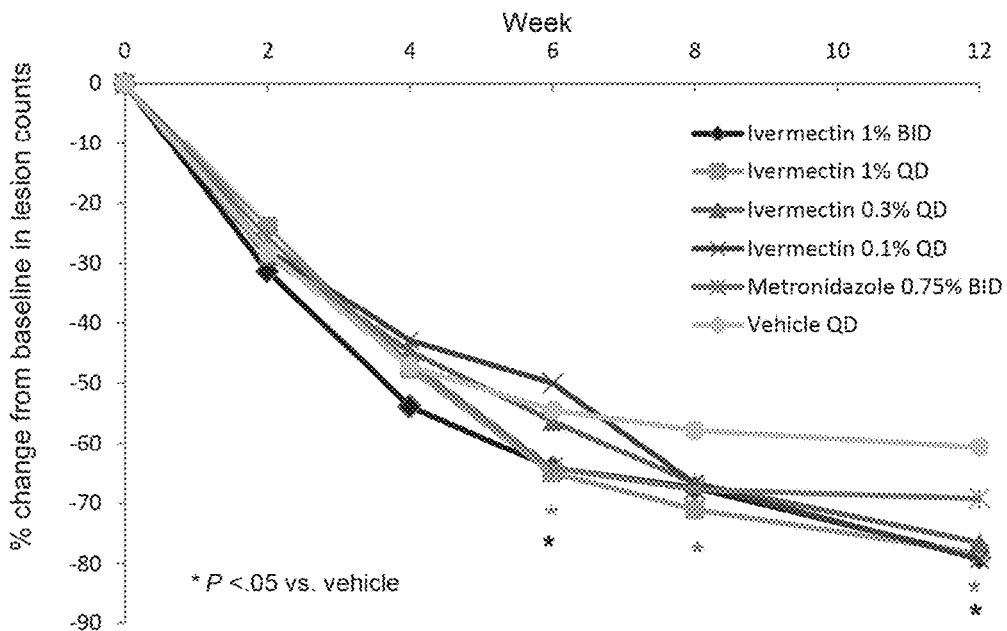
FIG. 1 shows the median percentage change from baseline in lesion counts (ITT-LOCF population) in a dose range study, after various topical treatments.

Various publications, articles and patents are cited or described in the background and throughout the specification; each of these references is herein incorporated by reference in its entirety. Discussion of documents, acts, materials, devices, articles, or the like which have been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural references unless the context clearly dictates otherwise.

Ivermectin is a member of the avermectin class, which has been shown in immunopharmacological studies to exert anti-inflammatory effects by inhibiting lipopolysaccharide-induced production of inflammatory cytokines, such as tumor necrosis factor alpha and interleukin (IL)-1b, while upregulating the anti-inflammatory cytokine IL-10[10]. It is a semi-synthetic derivative isolated from the fermentation of *Streptomyces avermitilis*, that belongs to the avermectin family of macrocyclic lactones. Ivermectin is a mixture containing 5-O-demethyl-22,23-dihydroavermectin Ala plus 5-O-demethyl-25-de(1-methylpropyl)-25-(1-methylethyl)-22,23-dihydroavermectin Ala, generally referred to as 22,23-dihydroavermectin B1a and B1b or H2B1a and H2B1b, respectively. The respective empirical formulas of H2B1a and H2B1b are $C_{48}H_{74}O_{14}$ and $C_{47}H_{72}O_{14}$ with molecular weights of 875.10 and 861.07 respectively.

Ivermectin is a macrocyclic lactone derivative, its therapeutic effect is thought to be prominently due to its anti-inflammatory properties, similar to that of other macrolides.[11-12] Avermectin has been reported to exert anti-inflammatory effects by inhibiting lipopolysaccharide-induced production of inflammatory cytokines. In addition to its anti-inflammatory mode of action, ivermectin possesses antiparasitic properties. Its predecessor, avermectin, is an antiparasitic agent of agricultural importance first isolated in 1974.[13] Several studies support ivermectin's role in the effective oral treatment of cutaneous demodicidosis (in combination with topical permethrin cream) and scabies, as well as topical treatment of head lice.[14-16] Ivermectin causes death of parasites, primarily through binding selectively and with high affinity to glutamate-gated chloride channels, which occur in invertebrate nerve and muscle cells. This leads to the interruption of nerve impulses, causing paralysis and death of parasitic organisms. Ivermectin is known to act on *Demodex* mites in localized and generalized demodicidosis in animals and in humans.

In the present invention, studies were conducted to evaluate the efficacy and safety of ivermectin in treating papulopustular rosacea (PPR). It was discovered that, as early as 2 weeks after the initial topical administration of a pharmaceutical composition comprising 0.5 to 1.5% (w/w) ivermectin to the subject, a significant reduction in inflammatory lesion count was observed.

As used herein, a "significant reduction" refers to a reduction that is statistically significant, not due to chance alone, which has a p-value of 0.05 or less. A "significant reduction" can have a p-value of less than 0.05, 0.04, 0.03, 0.01, 0.005, 0.001, etc. As used herein, "inflammatory lesion count" refers to the number of inflammatory lesions associated with rosacea or PPR. Inflammatory lesions can be papules and/or pustules. A papule is a small, solid elevation less than one centimeter in diameter, and a pustule is a small, circumscribed elevation of the skin, which contains yellow-white exudates.

The lesions can be, e.g., papules and/or pustules of any sizes (small or large). For example, at two weeks after the initial treatment, about 30% (p<0.001) and 27.3% (p<0.01) median reduction of the inflammatory lesion counts were observed from patients treated with ivermectin in two separate clinical studies using methods of the present invention. These reductions are statistically significant because they had p values less than 0.01 or even less than 0.001.

This early onset of significant effectiveness is unexpected and surprising in comparison with the conventional treatments. For example, significant treatment differences were only observed from week 4 or week 8 forward in two phase III studies for the topical treatment of moderate PPR using twice-daily 15% azelaic acid (Thiboutot et al., 2003, *J. Am Acad Dermatol*, 48 (6): 836-845), while no statistically significant difference with respect to the median inflammatory lesion counts or the median percentage change in inflammatory lesion counts was observed at any evaluation time during the study (P≥0.29) of topical treatment of moderate to severe PPR using once-daily 0.75% or 1.0% metronidazole (Dahl et al., 2001, *J. Am Acad Dermatol*, 45 (5): 723-730).

This early onset of significant effectiveness is also unexpected and surprising in view of the prior teaching, that topical treatment with ivermectin would be anticipated to require once- or twice-daily applications for as long as four weeks to achieve sufficient follicle penetration and effective miticidal activity; and that after ivermectin carries out its miticidal activity on skin *Demodex folliculorum* organisms, remnants of the dead mites still elicit some flushing and lesion formation until the cleanup processes of the body remove them, a process that requires six to eight weeks; and that conventional anti-rosacea medications, such as oral tetracycline and topical metronidazole, are suggested to be employed to suppress early flareups and to give early clinical response during the initial phase of ivermectin administration (see, e.g., U.S. Pat. No. 5,952,372).

Side-by-side clinical studies in the present invention also showed that methods according to embodiments of the present invention result in more effective treatment of PPR as well as longer time for the relapse of PPR to occur than the conventional topical treatment, such as that with metronidazole. In addition, methods according to embodiments of the present invention also result in less frequent adverse skin reactions than the conventional topical treatments.

While not wishing to be bound by the theory, it is believed that the mechanism of action of ivermectin in treating papulopustular rosacea may be linked to anti-inflammatory effects of ivermectin as well as the death of *Demodex* mites that have been reported to be a factor in inflammation of the skin. Because ivermectin has both anti-inflammatory and anti-parasitic activities, treatment of PPR with ivermectin represents an innovative therapy addressing these relevant pathogenic factors in PPR, thus a novel addition to the current treatment armamentarium.

According to an embodiment of the present invention, a method of treating papulopustular rosacea in a subject in need thereof, comprises topically administering to a skin area affected by the papulopustular rosacea a pharmaceutical composition comprising ivermectin and a pharmaceutically acceptable carrier.

As used herein, "pharmaceutically acceptable carrier" refers to a pharmaceutically acceptable vehicle or diluent comprising excipients and auxiliaries that facilitate processing of the active compounds into preparations which can be used pharmaceutically.

The pharmaceutical compositions according to the invention are suited for treating the skin. They can be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases. They can also be in the form of suspensions of microspheres or nanospheres or of lipid or polymeric vesicles or of polymeric patches and of hydrogels for controlled release. These compositions for topical application can be in anhydrous form, in aqueous form, or in the form of an emulsion.

In one embodiment of the present invention, the pharmaceutical composition being formulated as an emulsion, the topical pharmaceutical emulsion comprises ivermectin, and one or more other ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

In a preferred embodiment of the present invention, the pharmaceutical composition comprises 0.5-1.5% (w/w) ivermectin, more preferably, about 1% (w/w) ivermectin, and a pharmaceutically acceptable carrier.

In another preferred embodiment of the present invention, the pharmaceutical composition comprises about 1% (w/w) ivermectin, and one or more inactive ingredients selected from the group consisting of carbomer, such as carbomer copolymer type B; cetyl alcohol; citric acid monohydrate; dimethicone 20 Cst; edetate disodium; glycerin; isopropyl palmitate; methyl paraben; oleyl alcohol; phenoxyethanol; polyoxyl 20 cetostearyl ether; propylene glycol; propyl paraben; purified water; sodium hydroxide; sorbitan monostearate and stearyl alcohol.

As used herein, the term "subject" means any animal, preferably a mammal, most preferably a human, to whom will be or has been administered compounds or topical formulations according to embodiments of the invention. Preferably, a subject is in need of, or has been the object of observation or experiment of, treatment or prevention of papulopustular rosacea.

As known to those skilled in the art, an "intent-to-treat population" or "ITT population" refers to all subjects who are randomized in a clinical study and to whom the study drug is administered. "ITT-LOCF" refers to the ITT population using the Last Observation Carried Forward (LOCF) method, a standard method of handling missing data, which imputes or fills in values based on existing data. "ITT-MI" refers to the ITT population using the multiple imputations (MI) method based on all the data available in the model, another method for processing data known to those skilled in the art. A "per protocol population" or "PP population"

refers to subjects of the ITT population in a clinical study who have no major deviations from the protocol of study.

In one embodiment, "treatment" or "treating" refers to an amelioration, prophylaxis, or reversal of a disease or disorder, or of at least one discernible symptom thereof. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

Success of treating PPR can be measured using methods known in the art, such as by the reduction of inflammatory lesion count from the baseline before treatment, by an improvement from the baseline in an investigator's global assessment (IGA) score, or by both the reduction of inflammatory lesion count and the IGA score.

The IGA score is determined by a trained medical professional evaluating the skin condition of a patient utilizing an investigative global assessment of the skin condition. Typically, such global assessments assign a value to the degree of rosacea exhibited by the skin. In addition to the assessment made by the medical professional, the patient's input and observations of their skin condition and responses to various inquiries (e.g., stinging or burning sensations) also play a role in determining the IGA score that is assigned. For example, the IGA score for rosacea (Table 1) can range, for example, from 0 (clear) to 1 (almost clear) to 2 (mild) to 3 (moderate) to 4 (Severe), including values between these numeric gradings, such as 1.5, 2.6, 3.4 etc. (e.g., intervals of 0.1).

TABLE 1

Investigator's Global Assessment of Rosacea Severity

| Grade | Score | Clinical Description |
| --- | --- | --- |
| Clear | 0 | No inflammatory lesions present, no erythema |
| Almost Clear | 1 | Very few small papules/pustules, very mild erythema present |
| Mild | 2 | Few small papules/pustules, mild erythema |
| Moderate | 3 | Several small or large papules/pustules, moderate erythema |
| Severe | 4 | Numerous small and/or large papules/pustules, severe erythema |

In view of the present disclosure, a skin area that is affected by papulopustular rosacea can be identified using any diagnostic signs or means known in the art, and can be treated by methods according to embodiments of the present invention. Patients can have papulopustular rosacea at different stages, from mild to severe.

In a preferred embodiment, the patient has moderate to severe papulopustular rosacea. As used herein, a patient having "moderate to severe papulopustular rosacea" has at least moderate facial erythema and at least 10 papulopustular lesions before treatment. For example, the patient can have an IGA of rosacea of 3 or 4, and at least 10, 15, 20, 25 or more papulopustular lesions before treatment.

According to embodiments of the present invention, the papulopustular rosacea is treated by topically applying to a skin area affected by the papulopustular rosacea a pharmaceutical composition comprising ivermectin and a pharmaceutically acceptable carrier, and the treatment results in a reduction in the inflammatory lesion count from the baseline number of PPR lesions (before treatment) by at least 1 to 100 lesions or more, such as at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90 or 100 lesions or more. According to embodiments of the present invention, at least about 10%, 20%, 30%, 40%, 50%, 60%, 70%, 80%, 90% or 100% reduction in inflammatory lesion count is observed after the treatment. Depending on the number of inflammatory lesions, and other factors, such as the conditions of the patient, the treatment can last as long as it is needed, such as 4 to 12 weeks.

According to other embodiments of the present invention, the treatment reduces the IGA score in the treated subject. As used herein, the "success rate" in a clinical study refers to the percentage of subjects in the study having an IGA of 0 ("clear") or 1 ("almost clear") after the treatment.

According to embodiments of the present invention, the pharmaceutical composition can be topically administered once or twice daily, preferably once daily.

According to embodiments of the present invention, after the initial successful treatment with ivermectin, i.e., to an IGA of 0 or 1, it takes a longer time to relapse, i.e., to an IGA of 2 or above, as compared to the conventional treatments, such as topical treatment with 0.75% by weight metronidazole. For example, treatment with ivermectin (1%) once daily (QD) resulted in a statistically significant extended remission (e.g., delayed time to first relapse, and increase in the number of treatment free days) of rosacea when compared to metronidazole 0.75% BID in subjects who were successfully treated (IGA 0 or 1) for 16 weeks. There was also a numerical trend in favor of ivermectin 1% QD for the relapse rates.

As used herein, "time to first relapse" is defined as the time elapsed between initial successful treatment to an IGA of rosacea of 0 or 1 to the first reoccurrence of the IGA to 2 or more in a subject. According to embodiments of the present invention, the median time to first relapse is about 110, 115, 120, 125, 130, 135, 140, 145 or 150 days or more in subjects treated with ivermectin, with a p value of 0.05 or less.

Another aspect of the present invention relates to a method of treating inflammatory lesions of papulopustular rosacea in a subject in need thereof, comprising topically administering to a skin area affected by the inflammatory lesions of papulopustular rosacea a pharmaceutical composition comprising ivermectin and a pharmaceutically acceptable carrier.

Preferably the subject has moderate to severe PPR before the treatment. More preferably, the subject has at least 15 inflammatory lesions of PPR before the treatment.

In another preferred embodiment, at two weeks after the initial treatment, about 27% or more median reduction of the inflammatory lesion counts is observed from subjects treated with ivermectin, with a p value of 0.01 or less.

Preferably, the pharmaceutical composition comprises 0.5% to 1.5% by weight ivermectin, more preferably about 1% by weight ivermectin.

In an embodiment of the present invention, as early as 2 weeks after the initial administration of the pharmaceutical composition to the subject, significant reduction in the inflammatory lesion count in the subject is observed. In other embodiments of the present invention, the method results in more reduction of the inflammatory lesion count and longer relapse-free time of the inflammatory lesions of rosacea in the subject in comparison to that achieved by topically administering to the subject a second pharmaceutical composition comprising 0.75% by weight metronidazole.

This invention will be better understood by reference to the non-limiting examples that follow, but those skilled in the art will readily appreciate that the examples are only illustrative of the invention and the claims which follow thereafter.

Unless otherwise indicated, all percentages of the ingredients in the present application are percentages by weight (w/w).

Example 1: Topical Ivermectin Compositions

Examples of pharmaceutical compositions that can be used in the present invention are described in U.S. Pat. No. 8,415,311 and U.S. Pat. No. 8,470,788, which are incorporated herein by reference. Compositions useful in the present invention include, but are not limited to, the following:

Composition 1

| Ingredients | % by weight relative to the total weight of the Composition |
|---|---|
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 2.5 |
| Steareth-20 | 3.0 |
| Sorbitan stearate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Composition 2

| Ingredients | % by weight relative to the total weight of the Composition |
|---|---|
| Ivermectin | 1.00 |
| Glycerol | 4.0 |
| Acrylate C10-30 alkyl acrylate Crosspolymer | 0.15 |
| Methyl para-hydroxybenzoate | 0.2 |
| Disodium EDTA | 0.05 |
| Citric acid monohydrate | 0.05 |
| Isopropyl myristate | 4.0 |
| Cetyl alcohol | 3.0 |
| Stearyl alcohol | 2.0 |
| Self-emulsifiable wax | 0.8 |
| Palmitostearic acid | 0.5 |
| Steareth-20 | 2.0 |
| Sorbitan palmitate | 1.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Composition 3

| Ingredients | % by weight relative to the total weight of the Composition |
|---|---|
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 3.0 |
| Steareth-20 | 3.0 |
| Sorbitan palmitate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Composition 4

| Ingredients | % by weight relative to the total weight of the Composition |
|---|---|
| Ivermectin | 1.00 |
| Glycerol | 4.0 |
| Acrylate C10-30 alkyl acrylate Crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Composition 5

| Ingredients | % by weight relative to the total weight of the Composition |
|---|---|
| Ivermectin | 1.4 |
| Glycerol | 4.0 |
| Acrylate C10-30 alkyl acrylate Crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 2: Dosage Study on Topical Treatment of PPR with Ivermectin

A phase II, randomized, investigator-blinded, parallel-group, active- and vehicle-controlled study was conducted to determine the optimal concentration and dose regimen of topical ivermectin cream for the treatment of inflammatory lesions of rosacea, and evaluate efficacy and safety.

Eligible subjects were adults with PPR. The majority of the subjects had at least 15 facial inflammatory lesions and at least mild facial erythema based on IGA of rosacea severity. Table 2 shows the demographic and baseline clinical characteristics (ITT population) of the subjects:

TABLE 2

|  | Ivermectin 1% BID (N = 48) | Ivermectin 1% QD (N = 52) | Ivermectin 0.3% (N = 47) | Ivermectin 0.1% (N = 51) | Metronidazole 0.75% BID (N = 48) | Vehicle QD (N = 50) |
| --- | --- | --- | --- | --- | --- | --- |
| Gender, n (%) |  |  |  |  |  |  |
| Female | 39 (81.3) | 33 (63.5) | 29 (61.7) | 31 (60.8) | 34 (70.8) | 35 (70.0) |
| Male | 9 (18.8) | 19 (36.5) | 18 (38.3) | 20 (39.2) | 14 (29.2) | 15 (30.0) |
| Age, year |  |  |  |  |  |  |
| Mean ± SD | 50.9 ± 12.3 | 50.4 ± 14.5 | 53.4 ± 14.5 | 52.7 ± 13.8 | 52.2 ± 15.9 | 52.2 ± 14.4 |
| Phototype, n (%) |  |  |  |  |  |  |
| I | 7 (14.6) | 4 (7.7) | 6 (12.8) | 4 (7.8) | 3 (6.3) | 7 (14.0) |
| II | 28 (58.3) | 27 (51.9) | 20 (42.5) | 26 (51.0) | 29 (60.4) | 28 (56.0) |
| III | 12 (25.0) | 14 (26.9) | 17 (36.2) | 18 (35.3) | 14 (29.2) | 15 (30.0) |
| IV | 1 (2.1) | 7 (13.5) | 4 (8.5) | 3 (5.9) | 2 (4.1) | 0 |
| Inflammatory lesion, n (%) |  |  |  |  |  |  |
| Mean ± SD | 37.3 ± 39.0 | 35.8 ± 18.2 | 35.1 ± 20.5 | 31.1 ± 15.0 | 37.4 ± 23.9 | 35.8 ± 19.9 |
| Min, max | 16, 270 | 16, 93 | 14, 108 | 15, 79 | 15, 153 | 15, 120 |
| IGA, n (%) |  |  |  |  |  |  |
| 1 = Almost Clear | 2 (4.2) | 0 | 1 (2.1) | 1 (2.0) | 1 (2.1) | 1 (2.0) |
| 2 = Mild | 15 (31.3) | 20 (38.5) | 15 (31.9) | 18 (35.3) | 18 (37.5) | 12 (24.0) |
| 3 = Moderate | 28 (58.3) | 24 (46.2) | 21 (44.7) | 29 (56.9) | 21 (43.8) | 28 (56.0) |
| 4 = Severe | 3 (6.3) | 8 (15.4) | 10 (21.3) | 3 (5.9) | 8 (16.7) | 9 (18.0) |

The subjects were randomized to receive one of the following six (6) regimens for 12 weeks: ivermectin 0.1% (w/w) once-daily (QD), ivermectin 0.3% (w/w) QD, ivermectin 1% (w/w) QD, ivermectin 1% (w/w) twice-daily (BID), metronidazole gel 0.75% (w/w) BID, or vehicle QD. The 6 groups were comparable in terms of demographic and baseline disease characteristics (Table 1): majority were female, Caucasian, with a skin phototype II and a mean age of 51.9±14.2 years. On average, the subjects had 35.4±23.8 inflammatory lesions, and the majority (51.0%) had an IGA of 3 (moderate).

Inflammatory lesion (sum of papules and pustules) counts, rate of success [% subjects "clear" or "almost clear" based on Investigator's Global Assessment (IGA), a scale from 0 (clear) to 4 (severe)], erythema [from 0 (none) to 3 (severe)], telangiectasia [from 0 (none) to 3 (severe)], adverse events, and satisfaction questionnaire (at the end of the study) were determined during the study.

FIG. 1 shows the median percentage change from baseline in lesion counts (ITT-LOCF population).

At week 12, both ivermectin 1% (w/w) QD and BID were significantly more effective than vehicle QD in the ITT-LOCF analysis based on the percentage change from baseline in inflammatory lesion counts (median: −78.3% and −78.9% vs. −60.6%; both p<0.05) (FIG. 1); this was also confirmed in the PP analysis. Although ivermectin 1% (w/w) BID was significantly more efficacious than vehicle, its magnitude of effect was not greater than ivermectin 1% (w/w) QD. A numeric trend favoring ivermectin 1% QD compared with metronidazole 0.75% BID was also observed in terms of median % change from baseline in inflammatory lesion counts [−78.3% vs. −69.2% at Week 12 (ITT-LOCF)]; the sample size was not large enough to detect differences between these groups.

All ivermectin dose regimens led to a significantly greater success rate than vehicle (70.8%, 65.4%, 63.8% and 62.7% for ivermectin 1% BID, 1% QD, 0.3% QD and 0.1% QD, respectively, vs. 42.0% for vehicle at Week 12; all p<0.05). Furthermore, the success rate for Metronidazole was 62.5%.

No difference was observed in the change in erythema or telangiectasia between the active and control groups.

All regimens were safe and well-tolerated, with similarly low incidence of adverse events. There were no serious related AEs. The majority of related AEs were mild, transient and dermatologic in nature, the most frequent for the ivermectin groups being skin discomfort (4 subjects), skin burning sensation (4 subjects), and worsening of rosacea (3 subjects).

Figure 2:
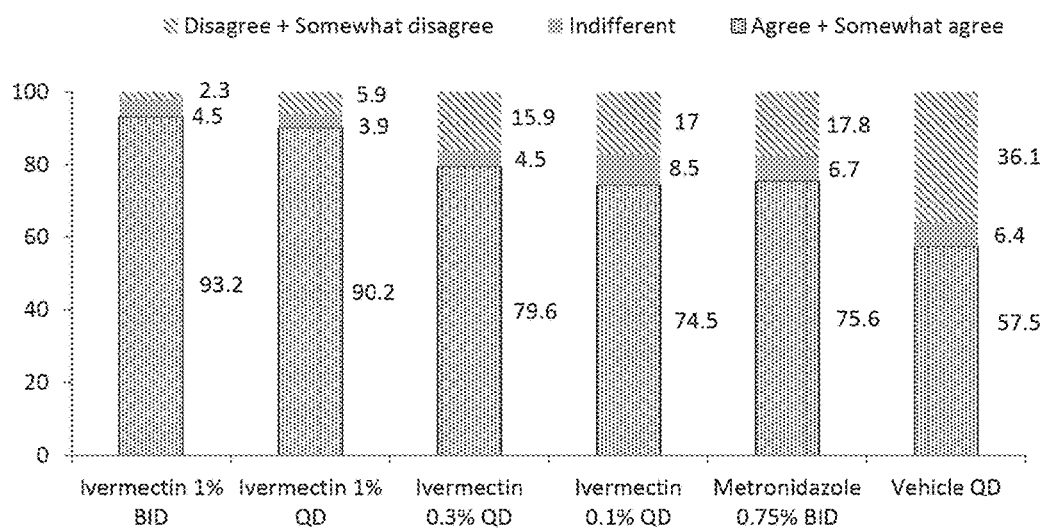
FIG. 2 illustrates subjects' response to the statement "the product improves my rosacea" after various topical treatments (ITT Observed)

FIG. 2 illustrates subjects' response to the statement "the product improves my rosacea" (ITT Observed). With increasing dosage of ivermectin, more subjects agreed with the statement "the product improves my rosacea" (FIG. 2) and were satisfied with the product (data not shown). The result was superior in ivermectin 1% QD and BID groups compared to the metronidazole 0.75% BID group. The majority of subjects in all Ivermectin groups considered that the product was easy to use (at least 95.5%), pleasant to use (at least 77.3%), and did not irritate the skin (at least 70.2%).

Topical administration of all tested ivermectin dose regimens (1% BID, 1% QD, 0.3% QD and 0.1% QD) led to a significantly greater success rate in treating PPR than vehicle; the result was superior in ivermectin 1% QD and BID groups compared to the metronidazole 0.75% BID group; and once daily topical administration of 1% (w/w) ivermectin was considered the optimal dose regimen, because it was safe, well tolerated, and provided significantly greater efficacy than vehicle for the treatment of PPR. Once daily topical administration is further preferred because it promotes better patient compliance.

Example 3: Efficacy and Safety Study of Ivermectin 1% Cream

To demonstrate the efficacy and safety of once-daily ivermectin 1% (w/w) cream in subjects with PPR, two identically designed randomized, double-blind, controlled studies were conducted (hereafter designated Study 1 and Study 2). Both studies were conducted in accordance with the ethical principles of the Declaration of Helsinki and Good Clinical Practices, and in compliance with local regulatory requirements.

Each study had three parts. In the first part of the study, subjects with PPR were treated with ivermectin 1% cream (IVM 1%) or vehicle once daily at bedtime for 12 weeks. In the second part of the study, subjects initially treated with IVM 1% once daily at bedtime continued the same treatment, while subjects treated with the vehicle once daily switched to topical treatment with azelaic acid 15% gel twice daily, in the morning and evening. The third part of the study consisted of 4 weeks safety follow-up, without treatment.

Figure 3:
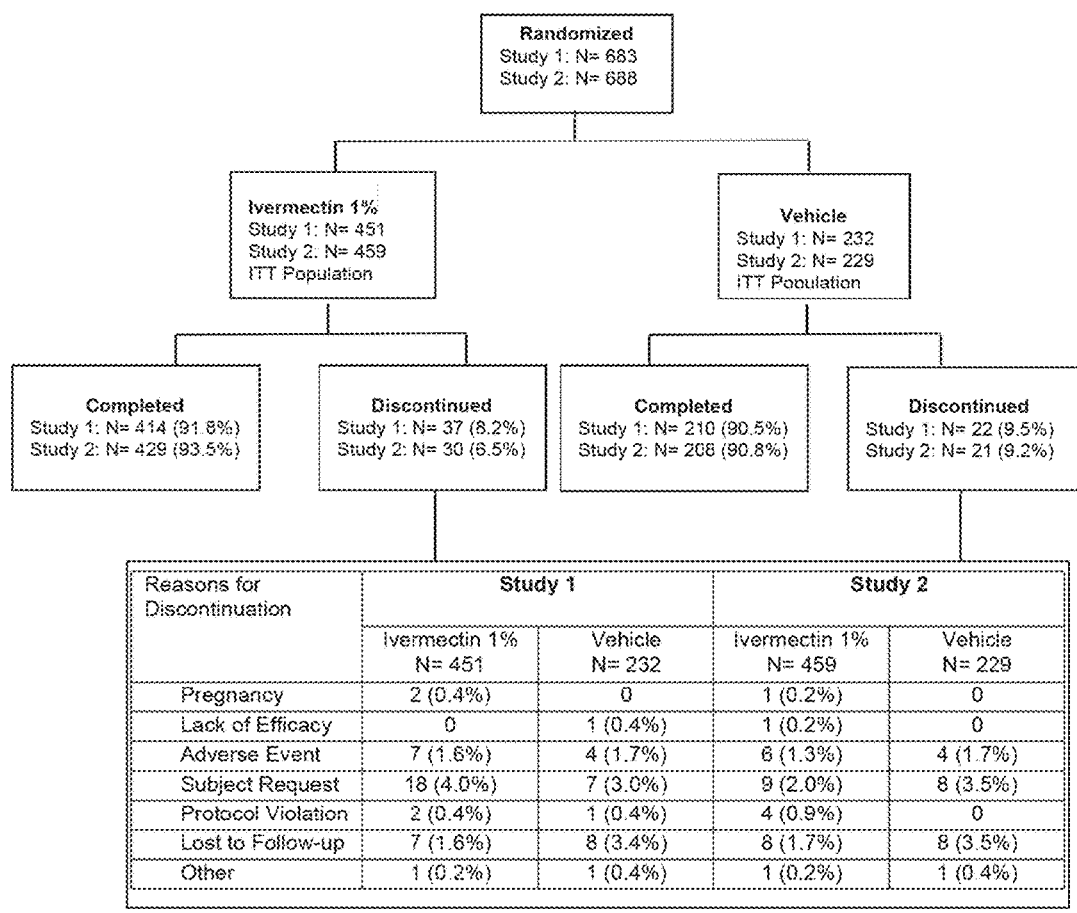
FIG. 3 shows subject disposition in 2 clinical studies on the safety and efficacy of ivermectin topical treatment.

Eligible subjects were 18 years or older, with moderate or severe papulopustular rosacea as noted by an IGA of 3 ("several small or large papules/pustules, moderate erythema") or 4 ("numerous small and/or large papules/pustules, severe erythema"), and presenting with 15-70 facial inflammatory lesions (papules and pustules). A total of 683 subjects with moderate to severe PPR were randomized in Study 1 (IVM 1%: 451, vehicle: 232), and 688 subjects in Study 2 (IVM 1%: 459, vehicle: 229) (FIG. 3).

Eligible subjects received either ivermectin cream 1% cream (once daily every day at bedtime) or vehicle cream (once daily every day at bedtime) on the entire face for 12 weeks. They were instructed to apply a thin film of cream on the entire face (right and left cheeks, forehead, chin and nose), e.g., in a pea-size amount of the cream, avoiding the upper and lower eyelids, lips, eyes and mouth. Subjects were also instructed to avoid rosacea triggers, such as sudden exposure to heat, certain foods, and excessive sun exposure. Study visits during the first study were as follows: screening visits, baseline, weeks 2, 4, 8, and 12 after the initial administration.

Efficacy assessments at each visit were the IGA of disease severity, and inflammatory lesion counts (papules and pustules) on each of the five facial regions (forehead, chin, nose, right cheek, left cheek). Safety assessments included adverse events (AEs) throughout the study, local tolerance parameters (stinging/burning, dryness, itching) at each study visit evaluated on a 4-point scale [from 0 (none) to 3 (severe)], and laboratory parameters (hematology and biochemistry) measured before and after treatment. Other assessments included the subject's evaluation of their rosacea improvement at the end of the study (week 12) compared to their condition at baseline, and two quality of life (QoL) questionnaires [a dermatology-specific instrument, the Dermatology Life Quality Index (DLQI)], 17 and a rosacea-specific instrument, the RosaQoL™18 completed at baseline and week 12.

The co-primary efficacy endpoints in both studies were the success rate based on the IGA outcome and absolute change from baseline in inflammatory lesion counts at the end of week 12 of the studies. The success rate based on IGA score [% of subjects who achieved "clear" or "almost clear" ratings on the IGA scale at week 12 (ITT-LOCF)] was analyzed by the Cochran-Mantel-Haenszel (CMH) test stratified by analysis site, using the general association statistic. The absolute change in inflammatory lesion counts from baseline to week 12 (ITT-LOCF) was analyzed by analysis of covariance (ANCOVA). Missing data at week 12 in the ITT population were imputed by the LOCF approach. Also, sensitivity analyses were conducted to impute missing data in order to assess the robustness of the primary efficacy results. The secondary efficacy endpoint was percent change in inflammatory lesion counts from baseline at week 12 (ITT-LOCF). The QoL questionnaires were analyzed using the Wilcoxon rank sum test, and other variables were descriptively analyzed. High mean scores from the QoL questionnaires indicated a low quality of life.

In Studies 1 and 2, the vast majority of subjects completed the study (91.4% and 92.6%, respectively). The treatment groups were similar at baseline in terms of demographics and baseline disease characteristics, with about 31-33 inflammatory lesions on average and the majority having moderate rosacea (Table 3). Most subjects were female (68.2% and 66.7% in Studies 1 and 2, respectively) and Caucasian/white (96.2% and 95.3%), with a mean age of 50.4 and 50.2 years, respectively. Additionally, treatment groups were comparable regarding rates/reasons for early study discontinuation (FIG. 3).

TABLE 3

Demographic and baseline clinical characteristics (ITT population)

| | | Study 1 Total (n = 683) | Study 2 Total (n = 688) |
|---|---|---|---|
| Age, years | Mean ± SD | 50.4 ± 12.09 | 50.2 ± 12.29 |
| | Min, Max | 19, 88 | 18, 89 |
| Gender, n (%) | Female | 466 (68.2%) | 459 (66.7%) |
| | Male | 217 (31.8%) | 229 (33.3%) |
| Race | White | 657 (96.2%) | 656 (95.3%) |
| | Black or African American | 9 (1.3%) | 10 (1.5%) |
| | Asian | 6 (0.9%) | 15 (2.2%) |
| | Other | 11 (1.6%) | 7 (1.0%) |
| Inflammatory lesion counts | Mean ± SD | 30.9 ± 14.33 | 32.9 ± 13.70 |
| IGA | 3 = Moderate | 560 (82.0%) | 403 (83.3%) |
| | 4 = Severe | 123 (18.0%) | 81 (16.7%) |

Figure 4A:
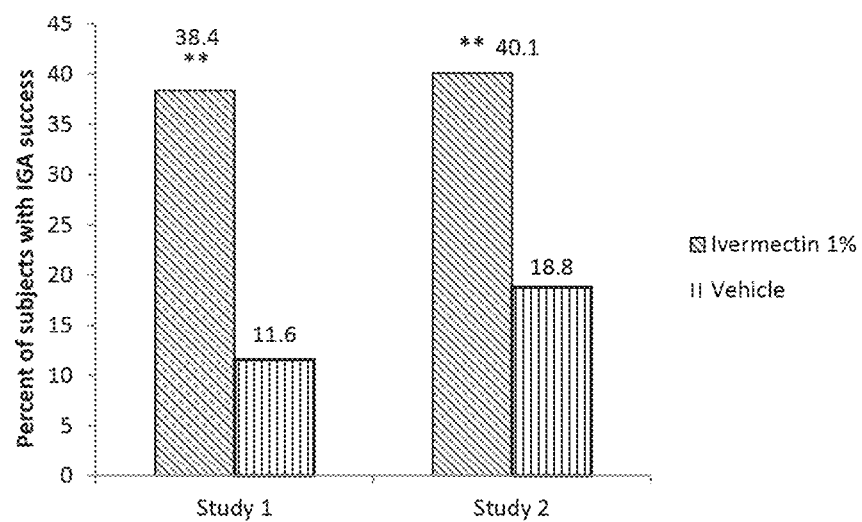
FIGS. 4A-4C illustrate proportions of subjects achieving IGA success ("clear" or "almost clear")
Figure 4B:
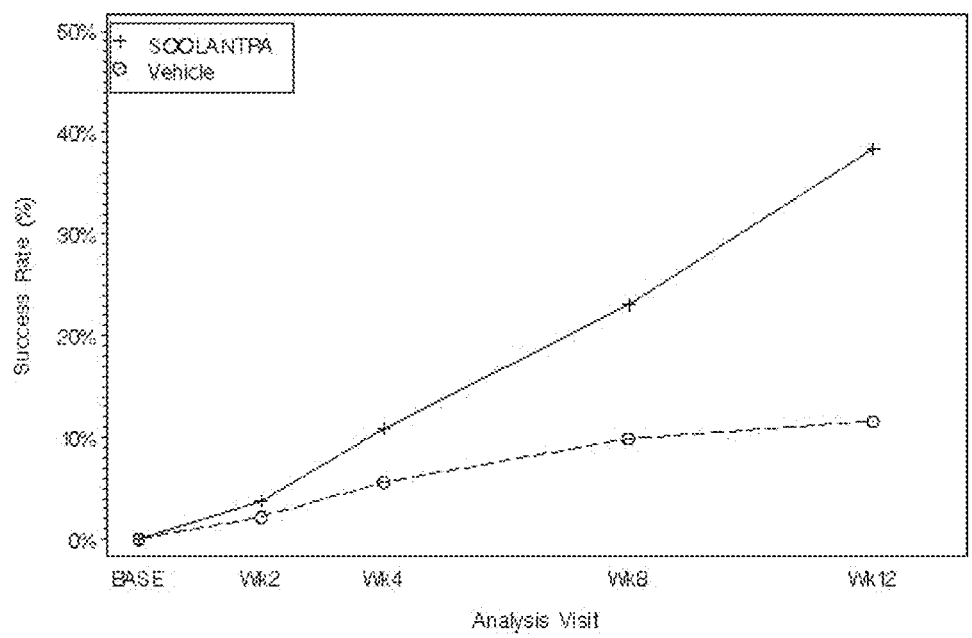
Figure 4C:
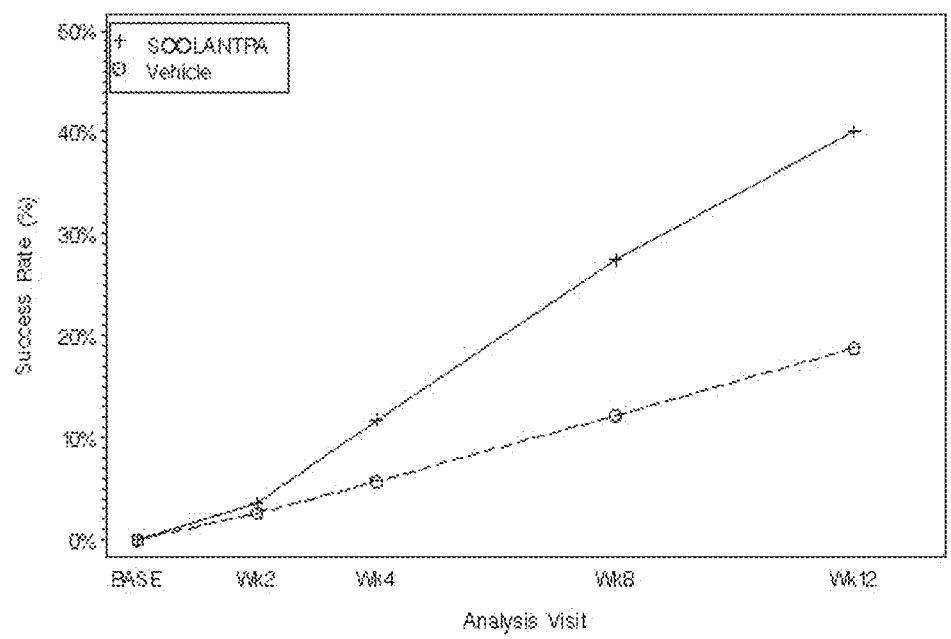

The proportion of subjects achieving IGA success ("clear" or "almost clear") at week 12 for Studies 1 and 2 were 38.4% and 40.1%, respectively for IVM 1% compared to 11.6% and 18.8% for vehicle (both p<0.001; FIG. 4A). A significant difference between treatment arms in both studies was observed based on IGA since week 4 (10.9% and 11.8% versus 5.6% and 5.7%, respectively; both p<0.05), and was sustained until Week 12 (FIGS. 4B and 4C).

Figure 5A:
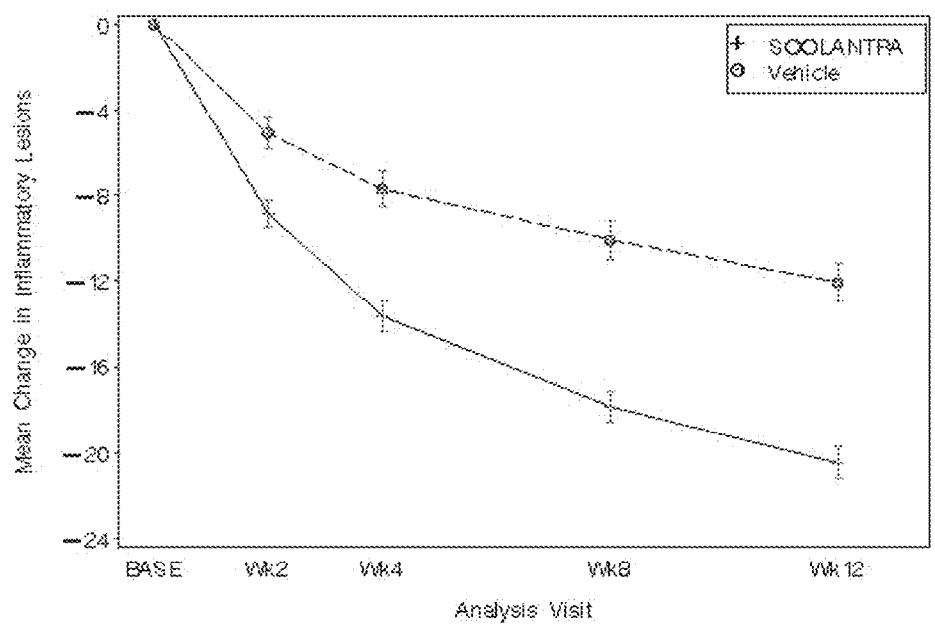
FIGS. 5A-5D show the change from baseline in inflammatory lesion counts (ITT-LOCF)
Figure 5B:
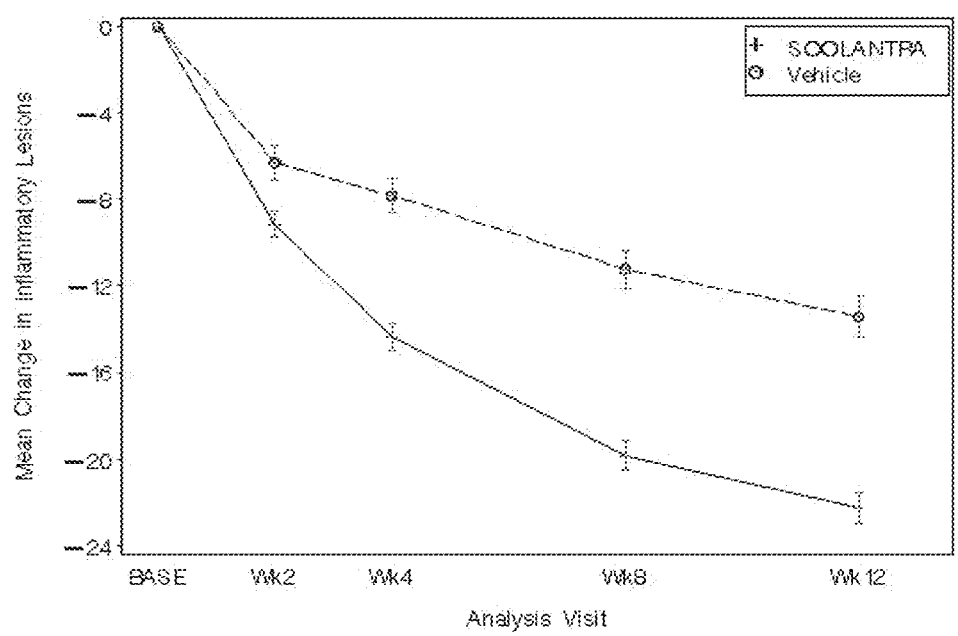
Figure 5C:
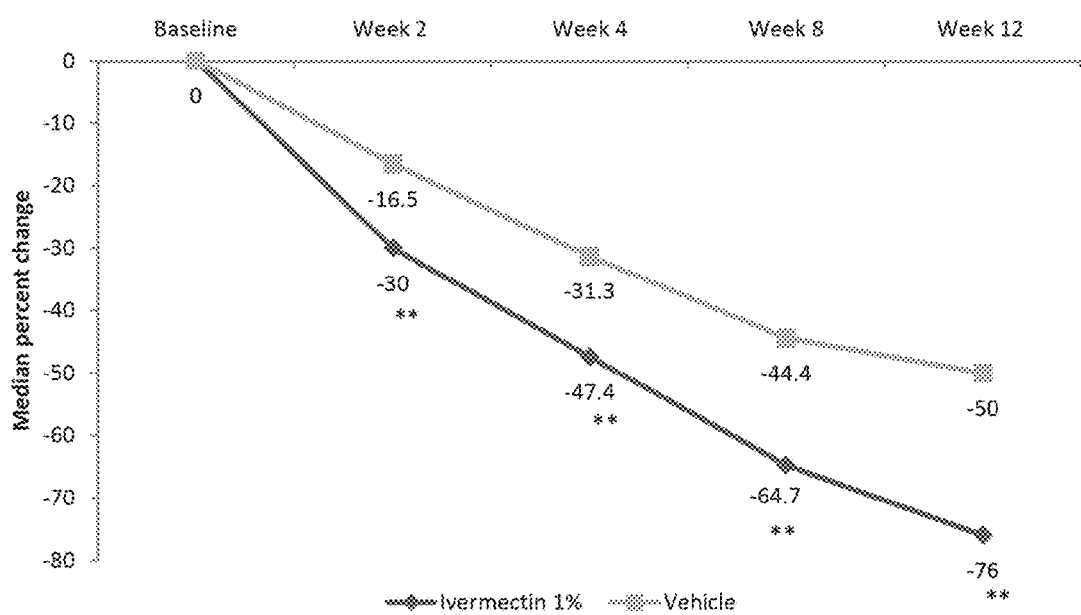
Figure 5D:
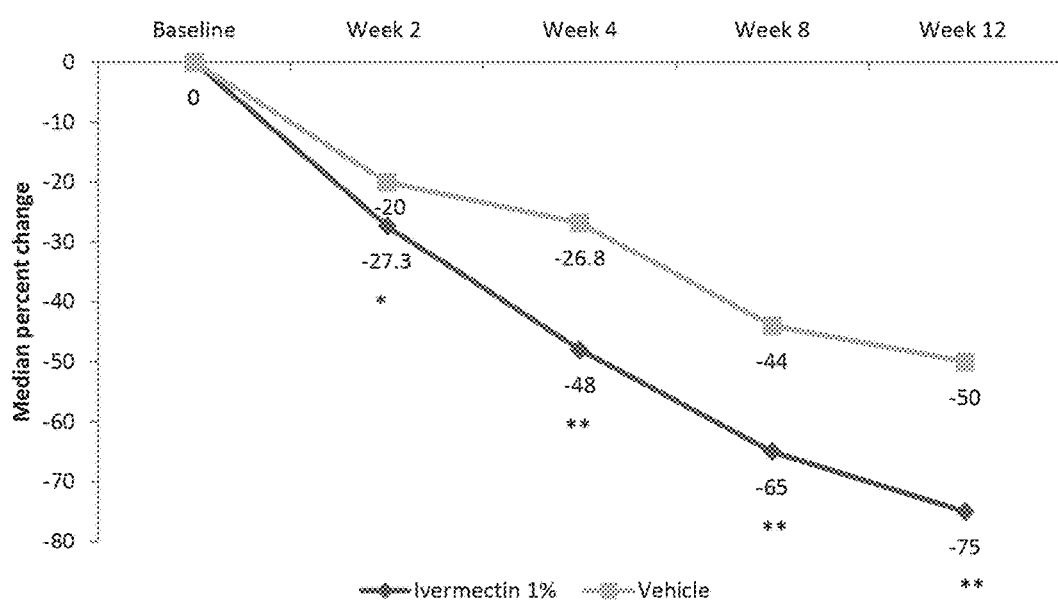

For inflammatory lesion counts, the mean difference between IVM 1% and vehicle from baseline to week 12 was −8.13 lesions for Study 1 and −8.22 for Study 2 (both p<0.001 versus vehicle), with a 95% CI of [−10.12, −6.13] and [−10.18, −6.25], respectively (FIGS. 5A and 5B). A mean reduction of 9 lesion counts was observed at week 2 in both studies when treated with IVM 1% (FIGS. 5A and 5B). Median reduction from baseline in inflammatory lesion counts for both studies was 76.0% and 75.0%, respectively, versus 50.0% for both vehicle groups at week 12 (p<0.001), with significant difference observed by week 2 at a median reduction of 30% and 27.3% (FIGS. 5C and 5D). This significant reduction in inflammatory lesion counts as early as week 2 was exceptional when compared with similar data from treatment with metronidazole or azelaic acid.

Table 4 summarizes efficacy outcomes of both studies at the end of the first part 12 week studies

|  | IVM 1% (N = 451) | Vehicle (N = 232) | IVM 1% (N = 459) | Vehicle (N = 229) |
|---|---|---|---|---|
| IGA |  |  |  |  |
| Number (%) of Subjects Clear or Almost Clear in the IGA at Week 12 | 173 (38.4) | 27 (11.6) | 184 (40.1) | 43 (18.8) |
| Inflammatory Lesions |  |  |  |  |
| Mean inflammatory lesion count at baseline | 31.0 | 30.5 | 33.3 | 32.2 |
| Mean inflammatory lesion count at Week 12 | 10.6 | 18.5 | 11.0 | 18.8 |
| Mean Absolute Change (%) in Inflammatory Lesion Count from Baseline at Week 12 | −20.5 (−64.9) | −12.0 (−41.6) | −22.2 (−65.7) | −13.4 (−43.4) |

The incidence of AEs was comparable between Studies 1 and 2 (40.5% and 36.5% for IVM 1% versus 39.4% and 36.5% for vehicle, respectively). Fewer subjects in IVM 1% groups tended to report related AEs than in vehicle groups (4.2% and 2.6% versus 7.8% and 6.5%, respectively), as well as for related dermatologic AEs (3.5% and 1.5% versus 6.9% and 5.7%) and related AEs leading to discontinuation (1.3% and 0.2%, versus 1.7% for both vehicle groups). A similarly low proportion of subjects reported serious AEs for IVM 1% and vehicle groups (0.7% and 1.5% versus 0.4% and 1.7%). There were no related serious AEs. The most common related AE in Study 1 was sensation of skin burning: 8 (1.8%) in IVM 1% subjects versus 6 (2.6%) for vehicle. For Study 2, the most common related AEs for IVM 1% were pruritis and dry skin (3 subjects each (0.7%)) compared to 0 and 2 subjects (0.9%) for vehicle, respectively. In addition, laboratory tests did not demonstrate clinically significant abnormalities.

At baseline before treatment application, a large proportion of subjects presented with local cutaneous symptoms consistent with rosacea, especially mild or moderate dry skin (for Studies 1 and 2, 63.0% and 57.0% for IVM 1%, and 59.3% and 60.0% for vehicle, respectively) and mild or moderate itching (57.3% and 49.4% for IVM 1%, and 45.4% and 49.1% for vehicle). At week 12 (last available data observed), the majority of subjects had none of the 2 cutaneous symptoms. A trend was observed in terms of absence of dryness in 83-86% of IVM 1% subjects versus 72-76% for vehicle, as well as for absence of itching in 82-85% for IVM 1% versus 70-78% for vehicle.

Figure 6A:
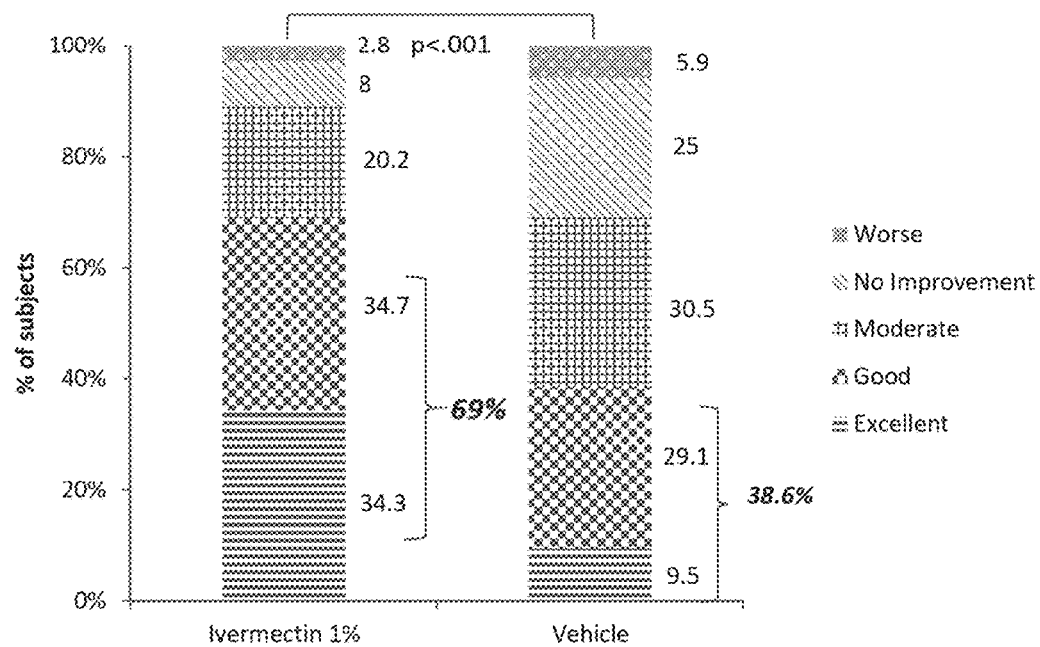
FIGS. 6A-6B show subjects' rating of rosacea improvement at week 12 from two studies.
Figure 6B:
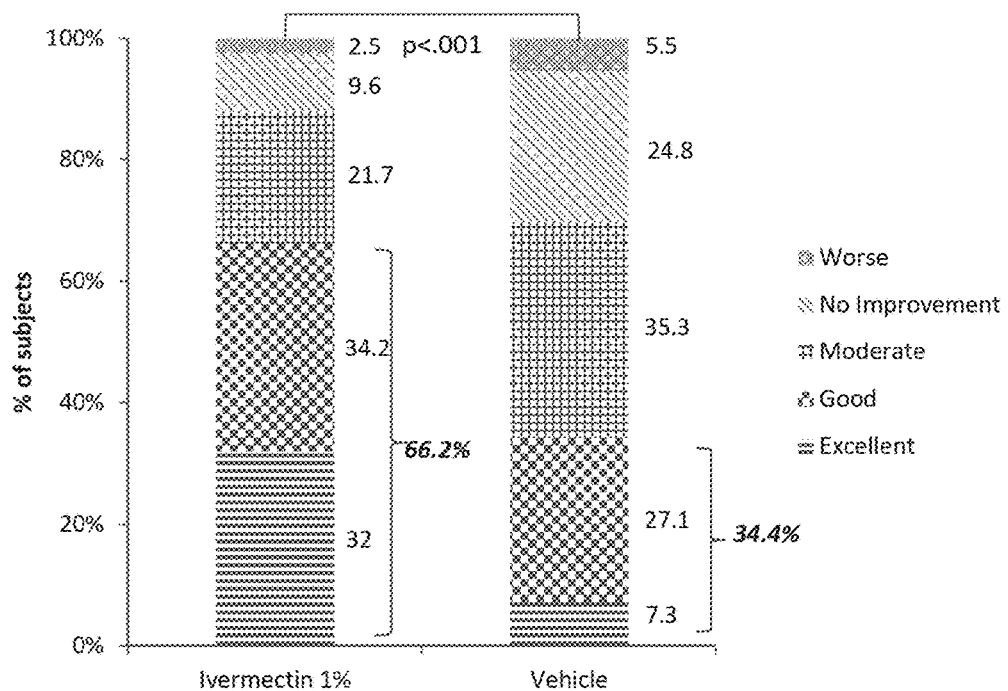
Figure 7:
FIG. 7 are photographs of a patient at Baseline and Week 12 (standard light)
Figure 7:

Improvement after treatment was rated by subjects as "excellent" or "good" by 69% and 66.2% for IVM 1% compared to 38.6% and 34.4% for vehicle (p<001), respectively (FIG. 6). "Excellent" improvement was reported by 34.3% and 32.0% for IVM 1% versus 9.5% and 7.3% for vehicle.

After 12 weeks of treatment, improved QoL scores were observed for subjects in the IVM 1% compared to vehicle groups. For the DLQI, it is of note that no difference between treatment groups was observed at baseline. At the end of each study, more subjects in the IVM 1% group (about 53%) than vehicle (about 35%) considered that their disease had no effect on their overall QoL (p<0.001). For RosaQoL™, improvement in QoL from baseline was higher in both studies for IVM 1% (−0.64±0.7 and −0.60±0.6 versus −0.35±0.5 for both vehicle groups (p<001 and p=0.001 for Studies 1 and 2, respectively). This result indicates that a higher proportion of subjects felt that their quality of life was not negatively impacted by rosacea in the group treated with IVM, compared to the control group treated with vehicle.

IGA was assessed during the second part of the studies (40 weeks). The percentages of subjects treated with IVM 1% achieving an IGA score of 0 or 1 continued to increase up to week 52, the end of the second part of the studies. The success rate (IGA=0 or 1) at week 52 was 71.1% and 76% in studies 1 and 2 respectively. In both studies, the incidences were comparable in the 2 groups of subjects treated by IVM 1% cream QD and azelaic acid 15% gel BID across the categories of related AEs, dermatologic AEs, serious AEs, related AEs leading to discontinuation, and AEs of special interests. There was no serious related AEs.

In the follow up third part of the studies, subjects treated with IVM 1% cream QD and azelaic acid 15% gel BID during the second part of the studies were comparable in reporting AEs. No subjects reported related serious AEs, related AEs leading to discontinuation.

The most frequent (>0.5% in any arm) AEs were skin disorders, and were less frequent with IVM 1% cream QD than azelaic acid 15% gel BID in both studies.

These two pivotal studies demonstrated the efficacy and safety of topical ivermectin 1% cream in the treatment of inflammatory lesions of rosacea with reproducibility. The effect was robust and highly significant (p, 0.001) in all primary and secondary endpoints at week 12 (ITT-LOCF). Onset of treatment effect was observed at week 4 in each study based on both IGA and lesion counts. Onset of treatment effect was observed at week 2 in each study based on lesion counts. The ivermectin 1% cream was well tolerated and safe in both studies. No notable difference was observed between the ivermectin 1% cream QD and corresponding vehicle and azelaic acid 15% gel BID. The most frequent (>0.5% in any arm) AEs were skin disorders, and were less frequent with IVM 1% cream QD than with the respective comparator. In addition, the continued daily application of the Ivermectin 1% Cream QD up to 1 year is well tolerated, with no unexpected safety findings associated with chronic use.

In conclusion, ivermectin, such as 1% ivermectin cream, was effective and safe in treating papulopustular rosacea.

Example 4: Comparison of the Efficacy and Safety of Ivermectin 1% Cream vs. Metronidazole 0.75% Cream This was an investigator-blinded, randomized, parallel group study comparing the efficacy and safety of ivermectin (hereafter designated IVM) 1% (w/w) cream vs. metronidazole 0.75% (w/w) cream with a 16-week period A and a 36-week period B to study recurrence. Study visits during Period A were as follows: a screening visit, and at baseline, weeks 3, 6, 9, 12 and 16.

Eligible subjects were 18 years or older, with moderate or severe papulopustular rosacea as noted by an IGA of 3 ("several small or large papules/pustules, moderate erythema") or 4 ("numerous small and/or large papules/pustules, severe erythema"), and presenting with 15-70 facial inflammatory lesions (papules and pustules).

Subjects were randomized in a 1:1 ratio to receive either IVM 1% cream (once daily, QD, at bedtime) or metronidazole 0.75% cream (twice daily, BID, as per labelling at morning and bedtime) for 16 weeks. Study drugs were applied in a thin film on the entire face (right and left cheeks, forehead, chin and nose), avoiding the upper and lower eyelids, lips, eyes and mouth. The subjects were instructed to maintain a consistent lifestyle throughout the study regarding rosacea triggers (i.e. avoiding environmental factors, certain foods, and excessive sun exposure).

terms of demographics and baseline disease characteristics, with about 32 inflammatory lesions on average and the majority having moderate rosacea (83.3% with an IGA of 3) (Table 5). As expected, the quantity of product applied in the metronidazole group (BID applications) was nearly twice as much as the product applied in the IVM 1% group (QD), with a mean of 1.31 g vs. 0.72 g, respectively.

TABLE 5

Demographic and baseline clinical characteristics (ITT population)

| | | Ivermectin 1% (n = 478) | Metronidazole 0.75% (n = 484) | Total (n = 962) |
|---|---|---|---|---|
| Age, years | Mean ± SD | 51.22 ± 13.40 | 51.87 ± 13.24 | 51.54 ± 13.32 |
| | Min, Max | 18, 85 | 18, 90 | 18, 90 |
| Gender, n (%) | Female | 311 (65.1%) | 316 (65.3%) | 627 (65.2%) |
| | Male | 167 (34.9%) | 168 (34.7%) | 335 (34.8%) |
| Race | Asian | 3 (0.6%) | — | 3 (0.3%) |
| | White | 475 (99.4%) | 484 (100.0%) | 959 (99.7%) |
| Skin Phototype | I | 18 (3.8%) | 17 (3.5%) | 35 (3.6%) |
| | II | 245 (51.3%) | 234 (48.3%) | 479 (49.8%) |
| | III | 178 (37.2%) | 213 (44.0%) | 391 (40.6%) |
| | IV | 36 (7.5%) | 19 (3.9%) | 55 (5.7%) |
| | V | 1 (0.2%) | 1 (0.2%) | 2 (0.2%) |
| Inflammatory lesion Counts | Mean ± SD | 32.87 ± 13.95 | 32.07 ± 12.75 | 32.46 ± 13.36 |
| Investigator Global Assessment | 3 = Moderate | 398 (83.3%) | 403 (83.3%) | 801 (83.3%) |
| | 4 = Severe | 80 (16.7%) | 81 (16.7%) | 161 (16.7%) |

Efficacy assessments at each visit were inflammatory lesion counts (papules and pustules) counted on five facial regions (forehead, chin, nose, right cheek, left cheek), and the Investigator's Global Assessment (IGA) of disease severity. Safety assessments included adverse events (AEs) throughout the study, local tolerance parameters (stinging/burning, dryness, itching) at each visit evaluated on a 4-point scale (from 0 (none) to 3 (severe)), and laboratory parameters measured at baseline, weeks 9 and 16. Other assessments included the subject's evaluation of rosacea improvement compared to their condition at baseline, and subject's appreciation questionnaire at the end of the study (regarding satisfaction with the study drug). Lastly, a quality of life questionnaire (Dermatology Life Quality Index (DLQI)) was completed at baseline and at the end of the study (week 16).

The ITT population included all subjects who were randomized and to whom the study drug was administered. The safety population included all subjects who received the study medication. The primary efficacy endpoint, percent change in inflammatory lesion counts from baseline to week 16, was analyzed using the CMH test stratified on center, with ridit transformation and row mean score difference statistic. Secondary efficacy endpoints included success rate (percent of subjects with IGA rated 0 ("clear") or 1 ("almost clear") (analyzed by CMH test stratified on center using general association statistic), IGA and absolute change in lesion counts (analyzed using ANCOVA, including treatments and analysis center as factors, and baseline as covariate). LOCF was the primary method for imputation of missing data, and multiple imputations (MI) method was used for sensitivity. Other variables were descriptively analyzed.

Figure 8:
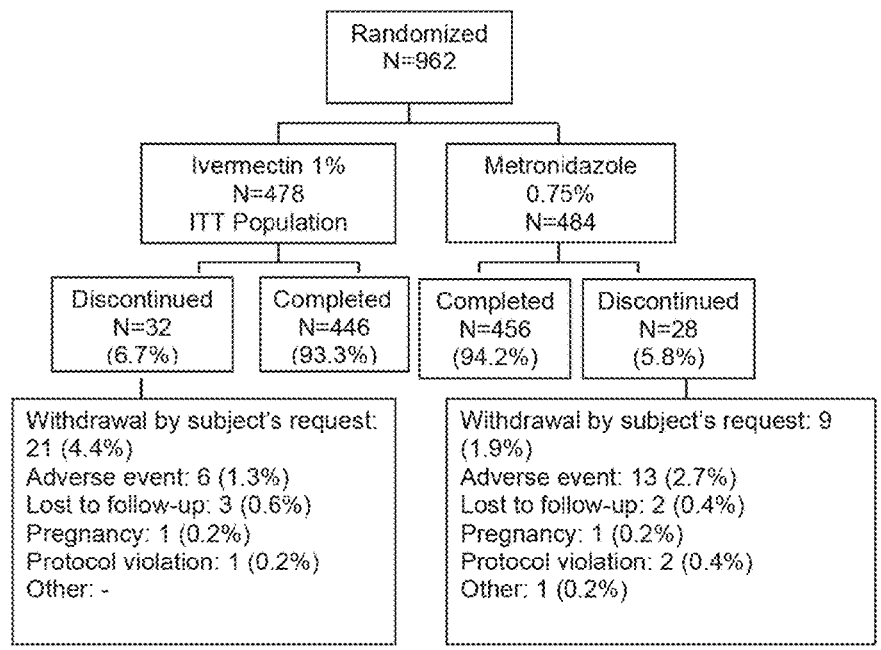
FIG. 8 shows subject disposition in a clinical study comparing the topical treatments with ivermectin and metronidazole.
Figure 9:
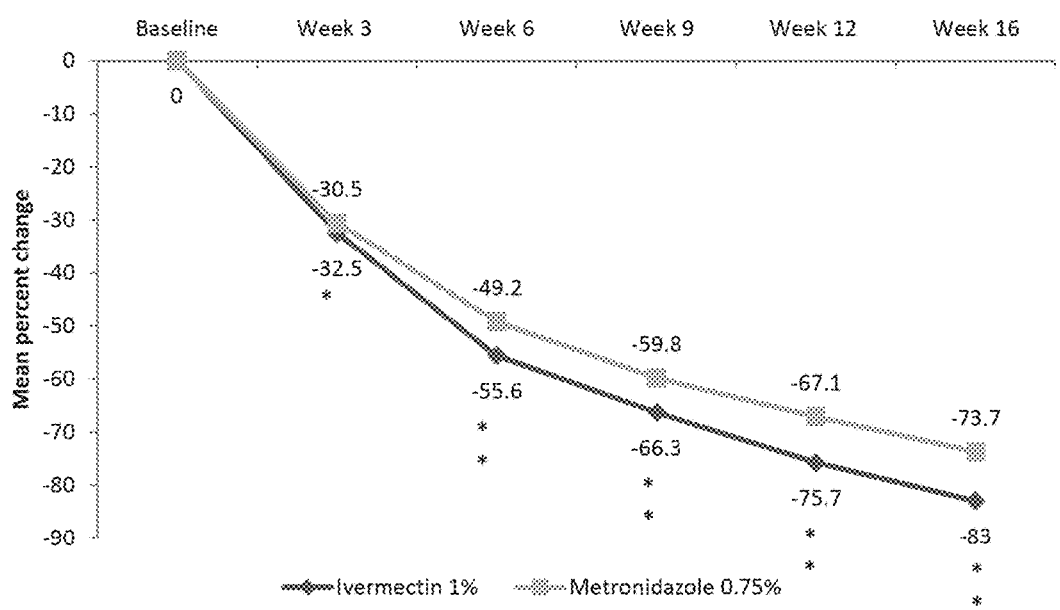
FIG. 9 illustrates the mean percent change from baseline in inflammatory lesion counts (ITT-LOCF) after the topical treatments with ivermectin and metronidazole, *p<0.05, **p<0.001.
Figure 10:
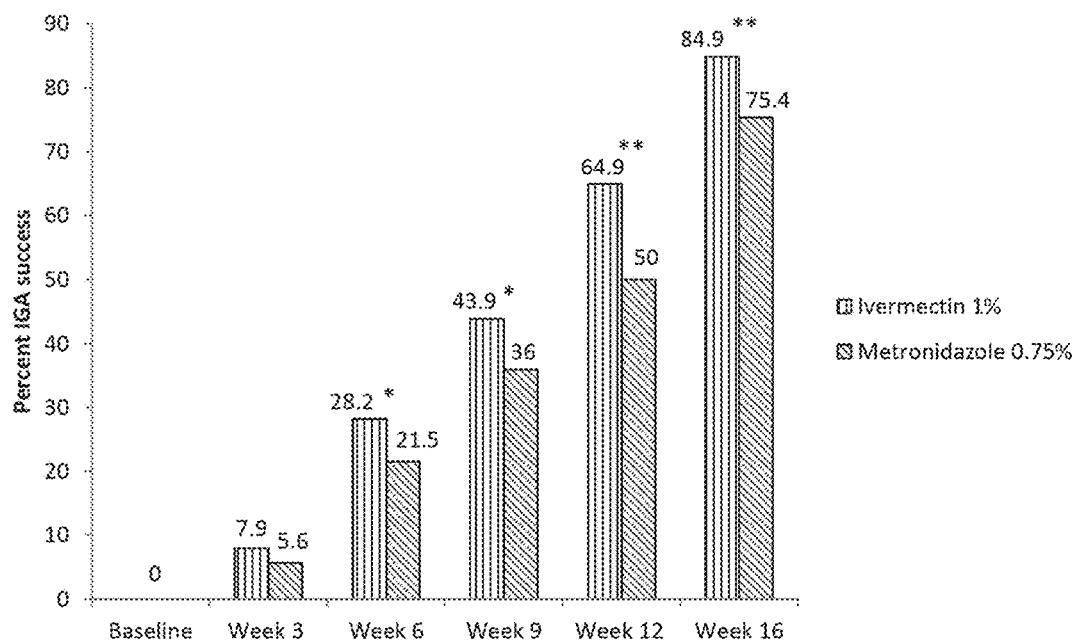
FIG. 10 shows the success rate based on IGA of "clear" or "almost clear" after the topical treatments with ivermectin and metronidazole, *p<0.05, **p<0.001.

A total of 1,034 subjects were screened and 962 randomized to receive IVM 1% cream (n=478) or metronidazole 0.75% cream (n=484); 902 (93.8%) completed the study (FIG. 8). Treatment groups were comparable at baseline in Regarding the primary endpoint, at week 16 (ITT-LOCF), IVM 1% cream was significantly superior to metronidazole 0.75% cream in terms of percent reduction from baseline in inflammatory lesion counts (83.0% vs. 73.7%; p<0.001; FIG. 9). This difference was observed as early as week 3 (ITT-LOCF) (as soon as week 6 with ITT-MI), and this continued through week 16 (all p-values≤0.04). It should be noted that in this study, there was no study visit or assessment prior to Week 3, thus the differences in treatment could have been observed earlier than week 3 if the first study visit was conducted earlier. Similar results were found for the IGA success rate (subjects rated "clear" or "almost clear"): 84.9% for IVM 1% cream vs. 75.4% for metronidazole 0.75% cream at week 16 (ITT-LOCF) (p<0.001). As illustrated in FIG. 10, the difference in IGA was the highest at week 12 (14.9% superior for ivermectin).

About 13% more subjects were rated as "clear" in terms of IGA for IVM 1% than metronidazole 0.75% (34.9% vs. 21.7%, respectively). Furthermore, in a subgroup analysis of success rate according to IGA severity, about 20% more subjects with severe rosacea at baseline in the IVM 1% group achieved success (82.5% vs. 63.0%).

The incidence of adverse events (AEs) was similar between groups (32.4% vs. 33.1% of subjects in the IVM 1% and metronidazole 0.75% groups, respectively), as well as for related AEs (2.3% vs. 3.7%). Furthermore, a comparably low number of subjects experienced a related dermatologic AE (9 subjects (1.9%) in the IVM 1% group and 12 (2.5%) in the metronidazole 0.75% group). The most common related AE was skin irritation (3 subjects (0.6%) vs. 4 subjects (0.8%) for IVM 1% and metronidazole 0.75%, respectively). Thirteen subjects reported serious but unrelated AEs. A total of 3 subjects (0.6%) in the IVM 1% group experienced related adverse events leading to discontinuation (due to skin irritation and hypersensitivity), compared to 10 (2.1%) subjects in the metronidazole 0.75% group (due to skin irritation, allergic dermatitis, aggravation of rosacea, erythema, pruritis, and general disorders (hot feeling)).

In terms of local tolerance, the incidence of worsening from baseline was higher in the metronidazole 0.75% group for stinging/burning (15.5% vs. 11.1%), dryness (12.8% vs. 10.0%), and itching (11.4% vs. 8.8%). Laboratory tests did not demonstrate clinically significant abnormalities.

Figure 11:
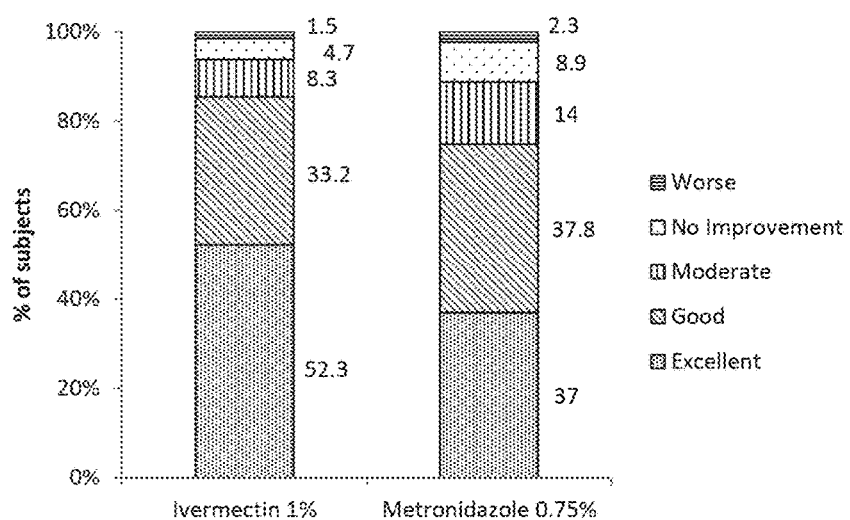
FIG. 11 shows subjects' rating of rosacea improvement after the topical treatments with ivermectin and metronidazole.

At the end of period A of this study, the majority (85.5%) of subjects in the IVM 1% group rated their global improvement as "excellent" or "good" compared to 74.8% in the metronidazole 0.75% group. Furthermore, more subjects receiving IVM 1% reported an "excellent" improvement of their rosacea (52.3% vs. 37.0%, respectively; FIG. 11). Regarding the subject's appreciation questionnaire, more subjects in the IVM 1% group were satisfied with the study drug (76.0% vs. 61.3% in the metronidazole 0.75% group). In addition, more subjects treated by IVM 1% tended to consider the product easy to use and that the time needed for application was satisfactory, whereas more subjects found metronidazole 0.75% to be irritating (data not shown).

At baseline, the mean DLQI scores were similar between groups (6.95 for IVM 1% and 6.05 for metronidazole 0.75%, respectively). Patients treated with IVM 1% showed a higher numerical decrease in their DLQI score than patients treated with metronidazole 0.75% (−5.18 vs. −3.92; p<0.01), indicating a higher improvement in quality of life. At the end of the study, 71% of patients treated with IVM 1% reported no effect at all on their quality of life (vs. 64% for metronidazole 0.75%), which means that a higher proportion of subjects felt that their quality of life was not negatively impacted by rosacea in the group treated with IVM, compared to the group treated with metronidazole. The study drugs diverged in favor of IVM 1% in the symptoms and feelings sub-scale (level of itching, soreness, pain or stinging: "not at all" for 78.7% vs. 63.0% in the metronidazole 0.75% group; level of embarrassment or self-consciousness: "not at all" for 70.3% vs. 60.1%, respectively).

Topical metronidazole 0.75% (w/w) has been one of the most frequently used therapies in the treatment of papulopustular rosacea. In this study, IVM 1% cream was significantly superior to metronidazole 0.75% cream in terms of percent reduction from baseline in inflammatory lesion counts, with an onset of efficacy (first difference vs. metronidazole 0.75%) as early as 3 weeks (or even earlier) that continued through 16 weeks. The findings show that ivermectin is more efficacious than metronidazole, with a tendency even in patients with higher lesion counts.

An overall good safety profile was observed for IVM, and it was well-tolerated in comparison with metronidazole. It is not surprising that for both products, patients experienced a similarly low number of related adverse events, particularly since the tolerability of metronidazole is known to be satisfactory. Metronidazole's higher incidence of worsening from baseline concerning stinging/burning, dryness, and itching may be attributed to the usual signs and symptoms of rosacea. Nevertheless, this affected the level of quality of life as measured by the DLQI, as more patients in the metronidazole group reported itching, soreness, pain or stinging.

Patient-reported outcomes for IVM 1% cream were consistent with its superior efficacy results. More patients using IVM indicated that the product was easy to use and that the time needed for application was satisfactory, implying that the daily application is more convenient than metronidazole's twice-daily regimen. Related to quality of life measures, fewer patients using IVM considered themselves to be embarrassed or self-conscious. Thus, ivermectin appears to be adapted to the complex etiology of rosacea, and in the study IVM 1% cream demonstrated superiority to metronidazole 0.75% cream in terms of inflammatory lesion reduction. As noted in the afore-mentioned Cochrane review, few robust studies have compared topical metronidazole with another rosacea treatment and in three identified studies, topical metronidazole was either non-significantly different or less effective than azelaic acid.[8] While metronidazole has been used in the past as a reasonable treatment for the papulopustular lesions of rosacea, its efficacy is surpassed by that of ivermectin along with the advantage of once-daily dosing.

The relapse among subjects successfully treated at the end of the Period A was studied during the treatment free Period B (36 weeks). At the end of Period A, only subjects with an IGA of "0" or "1" (clear or almost clear) were eligible for entering Period B. Then, their study treatment was discontinued and the subjects were followed for up to 8 months (36 weeks). In case of reoccurrence of an IGA of at least "2" (mild) at any time during Period B, the subjects were retreated with the same treatment received during the Period A. The re-treatment was stopped as soon as the IGA was back to "0" or "1" (clear or almost clear). The maximum duration of re-treatment was 16 consecutive weeks to mimic the Period A treatment duration. In order to characterize the relapses, the following parameters were assessed: (1) time of first relapse (time elapsed between Week 16 and first reoccurrence of IGA at "2", "3" or "4" inducing a retreatment course), (2) relapse rate (percentage of subjects with reoccurrence of IGA at "2", "3" or "4" after a period free of study treatment) and (3) number of days free of treatment.

At the start of Period B, treatment groups were comparable with respect to the demographic. Of the total 757 subjects included in Period B (399 in Ivermectin 1% and 358 in Metronidazole 0.75% groups, respectively), 504 (66.6%) were female, 754 (99.6%) were Caucasian and the mean age was 51.9 years. In terms of disease characteristics, the means inflammatory lesion counts were similar in both groups (median 2.0). But, the proportion of subjects with an IGA of 0 was higher in Ivermectin group than in Metronidazole group (41.6% versus 29.1%) due to the higher efficacy of Ivermectin treatment from Period A.

TABLE 6

End of Period A disease characteristics of subjects entering Period B

| | | Ivermectin | Metronidazole | TOTAL |
|---|---|---|---|---|
| Inflammatory lesion counts | N | 399 | 358 | 757 |
| | Mean | 2.58 | 2.96 | 2.76 |
| | SD | 3.20 | 3.42 | 3.31 |
| | Median | 2.00 | 2.00 | 2.00 |
| | Min~Max | 0~19 | 0~24 | 0~24 |
| | P25~P75 | 0~4 | 0~4 | 0~4 |
| Investigator Global Assessment | N | 399 | 358 | 757 |
| | 0 = Clear | 166 (41.6%) | 104 (29.1%) | 270 (35.7%) |
| | 1 = Almost Clear | 233 (58.4%) | 254 (70.9%) | 487 (64.3%) |
| Nodules | N | 399 | 358 | 757 |
| | 0 | 397 (99.5%) | 357 (99.7%) | 754 (99.6%) |
| | 1 | 2 (0.5%) | 1 (0.3%) | 3 (0.4%) |
| Papules | N | 399 | 358 | 757 |
| | Mean | 2.27 | 2.56 | 2.40 |
| | SD | 2.77 | 2.83 | 2.80 |
| | Median | 2.00 | 2.00 | 2.00 |
| | Min~Max | 0~16 | 0~17 | 0~17 |
| | P25~P75 | 0~4 | 0~4 | 0~4 |
| Pustules | N | 399 | 358 | 757 |
| | Mean | 0.32 | 0.40 | 0.36 |

TABLE 6-continued

End of Period A disease characteristics of subjects entering Period B

|  | Ivermectin | Metronidazole | TOTAL |
|---|---|---|---|
| SD | 0.91 | 1.20 | 1.06 |
| Median | 0.00 | 0.00 | 0.00 |
| Min~Max | 0~9 | 0~12 | 0~12 |
| P25~P75 | 0~0 | 0~0 | 0~0 |

The time to first relapse, defined as time elapsed between Week 16 and first reoccurrence of IGA at "2", "3" or "4" was analyzed following 2 definitions: (1) the first one was based on IGA only; and (2) the second one took also into account any major deviations by imputing relapse the day of first major deviation. For each definition, a sensitivity analysis was performed by imputing relapse 4 weeks after discontinuation for all subjects who discontinued early from Period B without relapse. Relapse rates followed the same convention analyses as the time to relapse.

Figure 12:
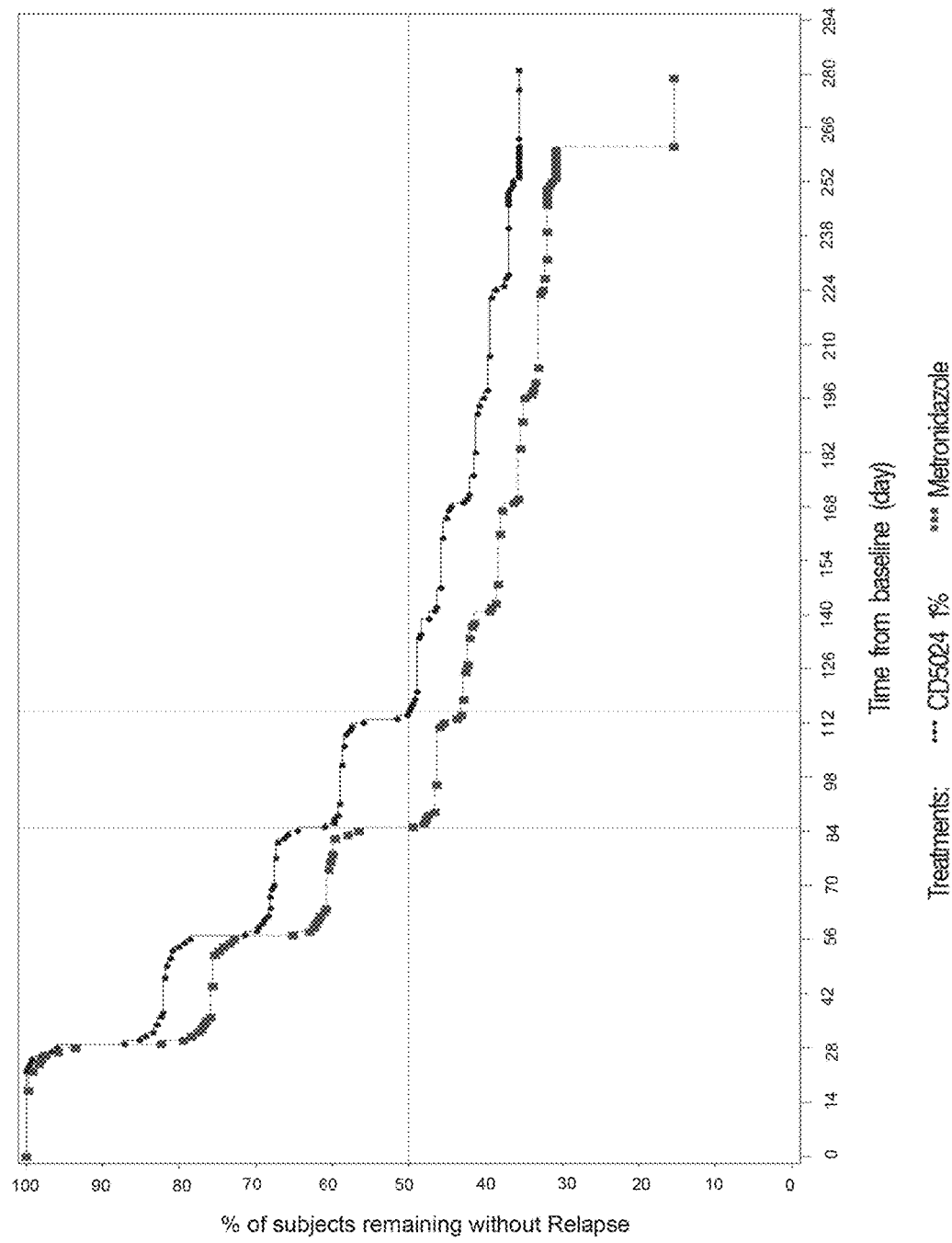
FIG. 12 shows time to first relapse defined as first re-occurrence of IGA≥2 after the successful treatments with ivermectin and metronidazole.

The median times to first relapse were 115 days for ivermectin 1% QD and 85 days for Metronidazole 0.75% BID (p=0.0365), the relapse rates were 62.7% and 68.4% respectively (Table 7). See also FIG. 12. When conducting the sensitivity analysis by imputing relapse 4 weeks later to subjects who discontinued early without relapse, the medians were 114 days and 85 days (p=0.0594) and the relapse rates were 66.2% and 70.4%, respectively. Similar results were obtained when taking also into account the day of first major deviation.

TABLE 7

|  | IVM 1% | Metronidazole | p-value (1) |
|---|---|---|---|
| N | 399 | 358 | 0.0365 |
| Median and 95% Confidence Interval | 115.0[113; 165] | 85.0[85; 113] | — |
| Mean ± Standard Error | 147.0 ± 4.66 | 133.6 ± 5.13 | — |

Relapse is based on IGA only
(1) Logrank test

Number of days free of treatment was defined for each subject enrolled in period B as the time interval between a visit where IGA is assessed as 0 or 1 and the next visit. The number of treatment-free days is the summation over all visits of period B meeting this criterion. An additional analysis was also performed by subtracting from the days free of treatment any time interval between visits when the subject while being IGA 0 or 1 had a major protocol deviation.

Based on IGA score showed a mean days free of treatment of 183 days for ivermectin 1% QD versus 170 days for metronidazole (p=0.026). When taking into account the protocol deviations the mean days free of treatment remained nearly the same 181 days versus 168 days (p=0.021) in favor of ivermectin 1% QD.

Ivermectin 1% cream QD treatment resulted in a statistically significant extended remission (i.e. delayed time to first relapse, and increase in the number of treatment free days) of rosacea when compared to Metronidazole 0.75% BID in subjects who were successfully treated (IGA 0 (clear) or 1 (almost clear)) for 16 weeks. There was also a numerical trend in favor of Ivermectin 1% cream QD for the relapse rates (62.7% and 68.4% in the Ivermectin 1% group and Metronidazole 0.75% group, respectively). It should be noted that the differences observed in favor of Ivermectin 1% in Period B are presumably the consequence of the higher efficacy of Ivermectin compared to Metronidazole observed at the end of Period A, with a higher proportion of subjects with an IGA=0 in the Ivermectin group (41.6% and 29.1% in Ivermectin and Metronidazole, respectively).

The overall pharmacoeconomic benefit of Ivermectin 1% cream QD versus Metronidazole 0.75% cream BID over the one year duration of the study (Period A & B), is considerable when viewed as the sum of the following elements: benefit of Ivermectin over Metronidazole observed at the end of Period A (84.9% of success in Ivermectin group vs. 75.4% in Metronidazole group), time to first relapse (115 vs. 85 days), relapse rate (62.7% vs. 68.4%) and number of days free of treatment (183.4 vs. 170.4).

REFERENCES

1. Wilkin J, Dahl M, Detmar M, et al. Standard classification of rosacea: Report of the National Rosacea Society Expert Committee on the classification and staging of rosacea. *J Am Acad Dermatol* 2002; 46:584-587.
2. Gupta M A, Gupta A K, Chen S J, Johnson A M. Comorbidity of rosacea and depression: an analysis of the National Ambulatory Medical Care Survey and National Hospital Ambulatory Care Survey—Outpatient Department data collected by the U.S. National Center for Health Statistics from 1995 to 2002. *Br J Dermatol* 2005; 153(6):1176-81.
3. Del Rosso J Q, Gallo R L, Tanghetti E, Webster G, Thiboutot D. An evaluation of potential correlations between pathophysiologic mechanisms, clinical manifestations, and management of rosacea. *Cutis* 2013; 91(3 Suppl):1-8.
4. Del Rosso J Q, Gallo R L, Kircik L, et al. Why is rosacea considered to be an inflammatory disorder? The primary role, clinical relevance, and therapeutic correlations of abnormal innate immune response in rosacea-prone skin. *J Drugs Dermatol* 2012; 11:694-700.
5. Steinhoff M, Buddenkotte J, Aubert J, et al. Clinical, cellular, and molecular aspects in the pathophysiology of rosacea. *J Investig Dermatol Symp Proc* 2011; 15:2-11.
6. Forton F, Seys B. Density of *Demodex folliculorum* in rosacea: a case-control study using standardized skin-surface biopsy. *Br J Dermatol* 1993; 128(6):650-9.
7. Karincaoglu Y, Bayram N, Aycan O, Esrefoglu M. The clinical importance of *demodex folliculorum* presenting with nonspecific facial signs and symptoms. *J Dermatol* 2004; 31(8):618-26.
8. van Zuuren E J, Kramer S F, Carter B R, Graber M A, Fedorowicz Z. Effective and evidence-based management strategies for rosacea: summary of a Cochrane systematic review. *Br J Dermatol* 2011; 165(4):760-81.
9. Elewski B E. Results of a national rosacea patient survey: common issues that concern rosacea sufferers. *J Drugs Dermatol* 2009; 8(2):120-3.
10. Ci X, Li H, Yu Q, Zhang X, Yu L, Chen N, et al. Avermectin exerts anti-inflammatory effect by downregulating the nuclear transcription factor kappa-B and mitogen-activated protein kinase activation pathway. *Fundam Clin Pharmacol* 2009; 23(4):449-55.
11. Yanagihara K, Kadoto J, Kohno S. Diffuse panbronchiolitis-pathophysiology and treatment mechanisms. *Int J Antimicrob Agents* 2001; 18 Suppl 1:S83-7.
12. Ianaro A, Ialenti A, Maffia P, Sautebin L, Rombola L, Carnuccio R, et al. Anti-inflammatory activity of macrolide antibiotics. *J Pharmacol Exp Ther* 2000; 292(1):156-63.

13. Campbell W C. History of avermectin and ivermectin, with notes on the history of other macrocyclic lactone antiparasitic agents. *Curr Pharm Biotechnol* 2012; 13(6): 853-65.
14. Forstinger C, Kittler H, Binder M. Treatment of rosacea-like demodicidosis with oral ivermectin and topical permethrin cream. *J Am Acad Dermatol* 1999; 41: 775-7.
15. Trendelenburg M, Buchner S, Passweg J, Raz Bravo A R, Gratwohl A. Disseminated scabies evolving in a patient undergoing induction chemotherapy for acute myeloblastic leukaemia. *Ann Hematol* 2001; 80(2):116-8.
16. Pariser D M, Meinking T L, Bell M, Ryan W G. Topical 0.5% ivermectin lotion for treatment of head lice. *N Engl J Med* 2012; 367(18):1687-93.
17. Finlay A Y, Khan G K. Dermatology Life Quality Index (DLQI)—a simple practical measure for routine clinical use. *Clin Exp Dermatol* 1994; 19(3): 210-6.
18. Nicholson K, Abramova L, Chren M M, Yeung J, Chon S Y, Chen S C. A pilot quality-of-life instrument for acne rosacea. *J Am Acad Dermatol* 2007; 57(2):213-21.
19. Zhang X, Song Y, Ci X et al. Ivermectin inhibits LPS-induced production of inflammatory cytokines and improves LPS-induced survival in mice. *Inflamm Res* 2008; 57:524-9.
20. Gerber P A, Buhren B A, Steinhoff M, Homey B. Rosacea: The cytokine and chemokine network. *J Investig Dermatol Symp Proc* 2011; 15(1):40-7.
21. Wolstenholme A J, Rogers A T. Glutamate-gated chloride channels and the mode of action of the avermectin/milbemycin anthelmintics. *Parasitology* 2005; 131 Suppl: S85-95.
22. Damian D. *Demodex* infestation in a child with leukemia: treatment with ivermectin and permethrin. *Int J Dermatol* 2003; 42:724-6.
23. Filho P A, Hazarbassanov R M, Grisolia A B et al. The efficacy of oral ivermectin for the treatment of chronic blepharitis in patients tested positive for *Demodex* spp. *Br J Ophthalmol* 2011; 95: 893-5.
24. Powell F C. Rosacea and the pilosebaceous follicle. *Cutis* 2004; 74 (3 Suppl): 9-12.
25. Marks R. The enigma of rosacea. *J Dermatol Treat* 2007; 18:326-8.
26. Forton F M N. Papulopustular rosacea, skin immunity and *Demodex: pityriasis folliculorum* as a missing link. *J Eur Acad Dermatol Venereol* 2012; 26:19-28.
27. Reinholz M, Ruzicka T, Schauber J. Cathelicidin L L-37: An antimicrobial peptide with a role in inflammatory skin disease. *Ann Dermatol* 2012; 24(2):126-135.
28. Millikan L. Rosacea as an inflammatory disorder: a unifying theory? *Cutis* 2004; 73(suppl 1): 5-8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating papulopustular rosacea in a subject in need thereof, comprising topically administering, once daily, to a skin area affected by the papulopustular rosacea a therapeutically effective amount of a pharmaceutical composition comprising ivermectin and a pharmaceutically acceptable carrier without co-administration of another active pharmaceutical ingredient, wherein the pharmaceutical composition comprises 0.5% to 1% by weight ivermectin, and a reduction in inflammatory lesion count in the subject is observed 2 weeks after the initial administration of the pharmaceutical composition.

2. The method of claim 1, wherein the subject has moderate to severe papulopustular rosacea before the treatment.

3. The method of claim 1, wherein the subject has 15 or more inflammatory lesions of the papulopustular rosacea before the treatment.

4. The method of claim 1, wherein the subject is treated once daily for 12 weeks or more.

5. The method of claim 1, wherein at least about 27.3% reduction of inflammatory lesion counts in the subject is observed by 2 weeks after the initial administration of the pharmaceutical composition.

6. The method of claim 5, wherein the pharmaceutical composition comprises about 1% by weight ivermectin.

7. The method of claim 1, wherein the pharmaceutical composition further comprises one or more ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

8. The method of claim 1, wherein the subject has no adverse reaction, and the adverse reaction is skin burning sensation or skin irritation.

9. The method of claim 4, wherein the subject has no adverse reaction, and the adverse reaction is skin burning sensation or skin irritation.

10. A method of treating inflammatory lesions of rosacea in a subject in need thereof, comprising topically administering, once daily, to a skin area affected by the inflammatory lesions of rosacea a pharmaceutical composition comprising ivermectin and a pharmaceutically acceptable carrier, without co-administration of another active pharmaceutical ingredient, wherein the pharmaceutical composition comprises 1% by weight ivermectin, wherein a reduction in inflammatory lesion count in the subject is observed 2 weeks after the initial administration of the pharmaceutical composition.

11. The method of claim 10, wherein the subject has moderate to severe papulopustular rosacea before the treatment.

12. The method of claim 10, wherein the subject has 15 or more of the inflammatory lesions before the treatment.

13. The method of claim 10, wherein the subject is treated once daily for 12 weeks or more.

14. The method of claim 13, wherein at least about 27.3% reduction of inflammatory lesion counts in the subject is observed by 2 weeks after the initial administration of the pharmaceutical composition.

15. The method of claim 10, wherein the pharmaceutical composition further comprises one or more ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

16. The method of claim 15, wherein the subject has moderate to severe papulopustular rosacea before the treatment.

17. The method of claim 15, wherein the subject has 15 or more of the inflammatory lesions before the treatment.

18. The method of claim 15, wherein the pharmaceutical composition comprises about 1% by weight ivermectin.

19. The method of claim 15, wherein about 27.3% or more reduction in inflammatory lesion counts in the subject is observed by 2 weeks after the initial administration of the pharmaceutical composition.

20. The method of claim 10, wherein the subject has no adverse reaction and the adverse reaction is skin burning sensation or skin irritation.

21. The method of claim 13, wherein the subject has no adverse reaction, wherein the adverse reaction is skin burning sensation or skin irritation.

22. A method of treating inflammatory lesions of rosacea in a subject in need thereof, comprising topically administering, once daily, to a skin area affected by the inflammatory lesions of rosacea a pharmaceutical composition comprising 1.0% by weight ivermectin and a pharmaceutically acceptable carrier, without co-administration of another active pharmaceutical ingredient, wherein the subject has no adverse reaction and the adverse reaction is skin burning sensation or skin irritation.

23. The method of claim 22, wherein a reduction in inflammatory lesion count in the subject is observed 2 weeks after the initial administration of the pharmaceutical composition.

24. The method of claim 23, wherein the subject has 15 or more inflammatory lesions of the papulopustular rosacea before the treatment.

25. The method of claim 24, wherein the pharmaceutical composition further comprises one or more ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

* * * * *